United States Patent
Musser et al.

(10) Patent No.: US 12,161,667 B2
(45) Date of Patent: *Dec. 10, 2024

(54) THERAPEUTIC CLAY COMPOSITIONS AND METHODS OF USING

(71) Applicant: ELANCO US INC., Greenfield, IN (US)

(72) Inventors: Robert Musser, Good Thunder, MN (US); Kim Friesen, Carthage, IN (US); Ran Song, Eden Prairie, MN (US)

(73) Assignee: ELANCO US INC., Greenfield, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/223,252

(22) Filed: Jul. 18, 2023

(65) Prior Publication Data

US 2024/0024358 A1    Jan. 25, 2024

Related U.S. Application Data

(63) Continuation of application No. 16/889,496, filed on Jun. 1, 2020, now Pat. No. 11,738,045.

(60) Provisional application No. 62/855,600, filed on May 31, 2019.

(51) Int. Cl.
*A61K 35/02*     (2015.01)
*A61P 15/00*    (2006.01)

(52) U.S. Cl.
CPC ............. *A61K 35/02* (2013.01); *A61P 15/00* (2018.01)

(58) Field of Classification Search
CPC ................................. A61K 35/02; A61P 15/00
See application file for complete search history.

(56) References Cited

FOREIGN PATENT DOCUMENTS

WO    WO-2018199748 A1 * 11/2018 ............. A23K 20/00

OTHER PUBLICATIONS

Reese et al. "Swine Nutrition Guide" Jul. 2000, pp. 1-41 (Year: 2000).*

* cited by examiner

*Primary Examiner* — Andrew S Rosenthal
(74) *Attorney, Agent, or Firm* — Barnes & Thornburg LLP

(57) ABSTRACT

The present invention provides methods of improve efficiency, growth, and performance in an animal by orally administering to the animal an effective amount of a therapeutic clay. The methods can reduce embryonic loss, increase litter size, increase the number of live births, improve the immune status of the maternal animal, reduce the concentration of maternal fecal amino acids, reduce the concentration of maternal fecal short-chained amino acid, increasing litter birth weight in the maternal animal, increase the amount of young animal colostrum intake, reduce young animal pre-weaning mortality, reduce the number of young animals lost due to low viability, reduce the number of weaned young animals, improve the immune status of young animals at weaning, reduce the number of lightweight young animals from nursery to market, increase the number of young animals marketed per sow, and increase calculated litter weight gain.

20 Claims, No Drawings

THERAPEUTIC CLAY COMPOSITIONS AND METHODS OF USING

CROSS REFERENCE TO RELATED APPLICATIONS

This application is a continuation application of U.S. patent application Ser. No. 16/889,496, filed Jun. 1, 2020, now U.S. Pat. No. 11,738,045, which claims priority to U.S. Provisional Patent Application No. 62/855,600, filed May 31, 2019, the contents of both of which are hereby incorporated by reference herein in their entirety.

FIELD OF THE INVENTION

The present invention generally relates to methods of using therapeutic clay, formulations comprising therapeutic clay, and methods of improving performance of an animal using the therapeutic clay.

BACKGROUND OF THE INVENTION

A number of artificial growth promoters are used extensively to control health challenges, enhance lean tissue gain, and improve growth, performance, and efficiency of feed utilization in livestock production. But use of artificial substances in livestock production has to become less prevalent as the market demands change. Therefore, the livestock industry is in need of alternative technologies to manage their herd health and production efficiency through all livestock growth production stages in the absence of artificial growth promoters. Optimally, this alternative growth promoter would be easy to implement on-farm and provide multiple benefits to herd health and production from birth to market.

SUMMARY OF THE INVENTION

One aspect of the disclosure encompasses a method of improving reproductive and litter performance of a maternal animal. The method comprises orally administering to the animal an effective amount of a therapeutic clay. In some aspects, the animal is a pig.

The clay can be formulated in a feed composition for oral administration to the animal. The clay can be administered during gestation, during lactation, and combinations thereof. For instance, the clay can be administered for a period of time during gestation. In some aspects, the clay is administered from breeding until farrowing. The clay can also be administered for a period of time during lactation. For instance, the clay can be administered from farrowing until weaning.

Improving reproductive performance can comprise reducing embryonic loss, increasing litter size, increasing the number of live births, improving the immune status of the maternal animal, reducing the concentration of maternal fecal amino acids, reducing the concentration of maternal fecal short-chained amino acid, and increasing litter birth weight. Improving the immune status of the maternal animal can comprise an increased level of IFNγ and TNF-α in the maternal animal, and decreased levels of TRAIL in the maternal animal. In some aspects, the level of pre-farrowing TNF-α in the maternal animal is positively correlated with total wean, negatively correlated with subsequent stillborns, and positively correlated with subsequent mummies. In some aspects, the level of pre-farrowing TRAIL is negatively correlated with subsequent total born and subsequent born alive. In some aspects, the level of wean IFN-γ is positively correlated with total wean.

Improving litter performance can comprise increasing the amount of young animal colostrum intake, reducing young animal pre-weaning mortality, reducing the number of young animals lost due to low viability, reducing the number of weaned young animals, improving the immune status of young animals at weaning, reducing the number of lightweight young animals from nursery to market, increasing the number of young animals marketed per sow, and increasing calculated litter weight gain. The immune status of young animals can comprise total immunoglobulins in blood.

The amount of clay in a feed composition can range from about 0.1 lb/ton to 10 lb/ton. The amount of clay in a gestation feed composition can range from about 0.5 lb/ton to 4.0 lb/ton. Further, the amount of clay in a lactation feed composition can range from about 0.5 lb/ton to 08 lb/ton.

Further, the amount of clay administered to a sow can range from about 1.0 g/d to about 10 g/d, from about 0.1 g/d to about 8 g/d, from about 0.5 g/d to about 3 g/d, or from about 4.0 g/d to about 7 g/d. Further, when the animal is a pig, the clay can be administered starting on day 3 to 93 of gestation.

Another aspect of the disclosure encompasses a method of increasing the amount of piglet colostrum intake, reducing pre-weaning mortality, reducing the number of piglets lost due to low viability, reducing the number of weaned pigs, reducing the number of lightweight pigs from nursery to market, increasing the number of pigs marketed per sow, and increasing calculated litter weight gain. The method comprises orally administering to a sow a therapeutically effective amount of a clay. In some aspects, the sow is parity 2 or parity 6 or more.

The clay can be formulated in a feed composition for oral administration to the animal. The clay can be administered during gestation, during lactation, and combinations thereof. For instance, the clay can be administered for a period of time during gestation. In some aspects, the clay is administered from breeding until farrowing. The clay can also be administered for a period of time during lactation. For instance, the clay can be administered from farrowing until weaning. In some aspects, when the animal is a pig, the clay is administered starting on day 3 to day 93 of gestation.

In some aspects, the amount of clay in a feed composition can range from about 0.1 lb/ton to 10 lb/ton. For instance, the amount of clay in a gestation feed composition can range from about 0.5 lb/ton to 4.0 lb/ton. The amount of clay in a lactation feed composition can range from about 0.5 lb/ton to 0.8 lb/ton.

The amount of clay administered to a sow can range from about 1.0 g/d to about 10 g/d, from about 0.1 g/d to about 8 g/d, from about 0.5 g/d to about 3 g/d, or from about 4.0 g/d to about 7 g/d. Further, when the animal is a pig, the clay can be administered starting on day 3 to 93 of gestation.

Another aspect of the disclosure encompasses method of reducing embryonic loss, increasing litter size, increasing the number of live births, improving the immune status of the maternal animal, reducing the concentration of maternal fecal amino acids, reducing the concentration of maternal fecal short-chained amino acid, and increasing litter birth weight. The method comprises orally administering to a sow an effective amount of a therapeutic clay. In some aspects, the sow is parity 2 or parity 6 or more.

The clay can be formulated in a feed composition for oral administration to the animal. The clay can be administered during gestation, during lactation, and combinations thereof.

For instance, the clay can be administered for a period of time during gestation. In some aspects, the clay is administered from breeding until farrowing. The clay can also be administered for a period of time during lactation. For instance, the clay can be administered from farrowing until weaning. In some aspects, the clay is administered starting on day 3 to day 93 of gestation.

In some aspects, the amount of clay in a feed composition can range from about 0.1 lb/ton to 10 lb/ton. For instance, the amount of clay in a gestation feed composition can range from about 0.5 lb/ton to 4.0 lb/ton. The amount of clay in a lactation feed composition can range from about 0.5 lb/ton to 0.8 lb/ton.

The amount of clay administered to a sow can range from about 1.0 g/d to about 10 g/d, from about 0.1 g/d to about 8 g/d, from about 0.5 g/d to about 3 g/d, or from about 4.0 g/d to about 7 g/d. Further, when the animal is a pig, the clay can be administered starting on day 3 to 93 of gestation.

Yet another aspect of the disclosure encompasses a method of enhancing pig litter performance. The method comprises orally administering an effective amount of a therapeutic day to a sow. In some aspects, the sow is parity 2, or parity 6 or more.

Enhancing litter performance can comprise increasing the amount of piglet colostrum intake, reducing pre-weaning mortality, reducing the number of piglets lost due to low viability, reducing the number of weaned pigs, improving the immune status of piglets at weaning, reducing the number of lightweight piglets from nursery to market, increasing the number of pigs marketed per sow, and increasing calculated litter weight gain.

The clay can be formulated in a feed composition for oral administration to the animal. The clay can be administered during gestation, during lactation, and combinations thereof. For instance, the clay can be administered for a period of time during gestation. In some aspects, the clay is administered from breeding until farrowing. The clay can also be administered for a period of time during lactation. For instance, the clay can be administered from farrowing until weaning. In some aspects, the clay is administered starting on day 3 to day 93 of gestation.

In some aspects, the amount of clay in a feed composition can range from about 0.1 lb/ton to 10 lb/ton. For instance, the amount of clay in a gestation feed composition can range from about 0.5 lb/ton to 4.0 lb/ton. The amount of clay in a lactation feed composition can range from about 0.5 lb/ton to 0.8 lb/ton.

The amount of clay administered to a sow can range from about 1.0 g/d to about 10 g/d, from about 0.1 g/d to about 8 g/d, from about 0.5 g/d to about 3 g/d, or from about 4.0 g/d to about 7 g/d. Further, when the animal is a pig, the clay can be administered starting on day 3 to 93 of gestation.

An additional aspect of the disclosure encompasses a method of enhancing reproductive performance of a sow, the method comprising administering to the sow an effective amount of a therapeutic clay. In some aspects, the sow is parity 2, or parity 6 or more.

Improving reproductive performance can comprise reducing embryonic loss, increasing litter size, increasing the number of live births, improving the immune status of the maternal animal, reducing the concentration of maternal fecal amino acids, reducing the concentration of maternal fecal short-chained amino acid, and increasing litter birth weight.

The clay can be formulated in a feed composition for oral administration to the animal. The clay can be administered during gestation, during lactation, and combinations thereof. For instance, the clay can be administered for a period of time during gestation. In some aspects, the clay is administered from breeding until farrowing. The clay can also be administered for a period of time during lactation. For instance, the clay can be administered from farrowing until weaning. In some aspects, the clay is administered starting on day 3 to day 93 of gestation.

In some aspects, the amount of clay in a feed composition can range from about 0.1 lb/ton to 10 lb/ton. For instance, the amount of clay in a gestation feed composition can range from about 0.5 lb/ton to 4.0 lb/ton. The amount of clay in a lactation feed composition can range from about 0.5 lb/ton to 0.8 lb/ton.

The amount of clay administered to a sow can range from about 1.0 g/d to about 10 g/d, from about 0.1 g/d to about 8 g/d, from about 0.5 g/d to about 3 g/d, or from about 4.0 g/d to about 7 g/d. Further, when the animal is a pig, the clay can be administered starting on day 3 to 93 of gestation.

One aspect of the present disclosure encompasses a method of improving pig litter performance, the method comprising orally administering an effective amount of a therapeutic clay to a sow. Improving litter performance can comprise increasing amount of young animal colostrum intake, reducing young animal pre-weaning mortality, reducing the number of young animals lost due to low viability, reducing the number of weaned young animals, improving the immune status of young animals at weaning, reducing the number of lightweight young animals from nursery to market, increasing the number of young animals marketed per sow, and increasing calculated litter weight gain.

The clay can be formulated in a feed composition for oral administration to the animal. The clay can be administered during gestation, during lactation, and combinations thereof. For instance, the clay can be administered for a period of time during gestation. In some aspects, the clay is administered from breeding until farrowing. The clay can also be administered for a period of time during lactation. For instance, the clay can be administered from farrowing until weaning. In some aspects, the clay is administered starting on day 3 to day 93 of gestation.

In some aspects, the amount of clay in a feed composition can range from about 0.1 lb/ton to 10 lb/ton. For instance, the amount of clay in a gestation feed composition can range from about 0.5 lb/ton to 4.0 lb/ton. The amount of clay in a lactation feed composition can range from about 0.5 lb/ton to 0.8 lb/ton.

The amount of clay administered to a sow can range from about 1.0 g/d to about 10 g/d, from about 0.1 g/d to about 8 g/d, from about 0.5 g/d to about 3 g/d, or from about 4.0 g/d to about 7 g/d. Further, when the animal is a pig, the clay can be administered starting on day 3 to 93 of gestation.

DETAILED DESCRIPTION OF THE INVENTION

The present disclosure is directed to methods of using therapeutic clay to improve efficiency, growth, and performance in animal production. Specifically, it was discovered that orally administering a therapeutic clay to an animal improves reproductive performance and litter performance in a mammalian animal. Surprisingly, administering the clay to a maternal animal improves performance of the litter even after weaning the young animals, and without administering the clay to the weaned animals. For instance, administering the clay to a maternal animal reduces the number of lightweight young animals from nursery to market and increases the number of young animals marketed per sow, even though the animals are not administered the clay.

I. Therapeutic Clay

In one aspect, the present disclosure provides a therapeutic clay. The clay is administered orally. In some aspects, the clay is formulated with other ingredients to facilitate oral administration and effective use. For instance, the therapeutic clay may be formulated with nutritive or other pharmaceutical agents for administration to an animal. The clay and formulations comprising the therapeutic clay are described below.

A. Clay

The term "clay" as used herein refers to a fine-grained natural rock or soil material that combines one or more clay minerals with traces of metal oxides and organic matter. Clays from natural geologic clay deposits are mostly composed of silicate minerals containing variable amounts of water trapped in the mineral structure. Additionally, as it will be recognized by an individual skilled in the art, clay may further comprise various amounts of metal oxides, organic matter, and other materials that can be mixed in with the clay. Sometimes clays comprise varying amounts of iron, magnesium, alkali metals, alkaline earths and other cations. Depending on the content of the soil, clay can appear in various colors, from white to dull gray or brown to a deep orange-red. Clays may be broadly classified into swelling clays, non-swelling days, and mixed layer clays.

Any clay may be used in a composition or method of the present disclosure, provided the clay has therapeutic properties. Without wishing to be bound by theory, therapeutic properties of the clay may include antimicrobial properties, antitoxin properties, as well as other properties that may contribute to the therapeutic properties of the clay distinct from antimicrobial to antitoxin activity. Conversely, a therapeutic clay can provide the desired therapeutic qualities without having antimicrobial properties or antitoxin properties. In some aspects, a therapeutic clay has therapeutic properties of the clay distinct from antimicrobial to antitoxin activity. A clay having therapeutic properties suitable for a method of the disclosure can be as described in U.S. patent application Ser. No. 15/266,570, the disclosure of which is incorporated herein by reference in its entirety.

In some aspects, a therapeutic clay can be combined with other clays. For instance, the therapeutic clay can be combined with other clays at a ratio of about 1:99 therapeutic clay to other clays, to about 99:1 therapeutic clay to other clays; at a ratio of about 80:20 therapeutic clay to other clays, to about 30:70 therapeutic clay to other clays; or at a ratio of about 45:55 therapeutic clay to other clays. In some aspects, the therapeutic clay can be combined with a bentonite clay.

A therapeutic clay may be a swelling clay, a non-swelling clay, a mixed layer clay, or a combination of a swelling clay, a non-swelling clay, and a mixed layer clay. In some aspects, the clay of the present disclosure is a swelling clay. Swelling or expansive clays are clays prone to large volume changes (swelling and shrinking) that are directly related to changes in water content. Swelling clays are generally referred to as smectite clays. Smectite clays have approximately 1-nm thick 2:1 layers (c-direction of unit cell) separated by hydrated interlayer cations which give rise to the clay's swelling. The "a" and "b" dimensions of the mineral are on the order of several microns. The layers themselves are composed of two opposing silicate sheets, which contain Si and Al in tetrahedral coordination with oxygen, separated by an octahedral sheet that contains Al, Fe and Mg in octahedral coordination with hydroxyls. The surfaces of the 2:1 layers (two tetrahedral sheets with an octahedral sheet in between) carry a net negative charge that is balanced by interlayer cations. The charged surfaces of the 2:1 layers attract cations and water, which leads to swelling.

Smectite clays may be classified with respect to the location of the negative charge on the 2:1 layers, and based on the composition of the octahedral sheet (either dioctahedral or trioctahedral). Dioctahedral smectites include beidellite having the majority of charge in the tetrahedral sheet, and montmorillonite having the majority of charge in the octahedral sheet. Similar trioctahedral smectites are saponite and hectorite. Swelling and other properties of smectite can be altered by exchanging the dominant interlayer cation. For example, swelling can be limited to 2 water layers by exchanging Na for Ca.

Smectite clays may be naturally mined. Alternatively, smectite clays may be synthesized. Methods of synthesizing smectite clays may be as described in U.S. Pat. No. 4,861,584, the disclosure of which is incorporated by reference herein in its entirety.

In other aspects, a therapeutic clay of the present disclosure is a non-swelling clay, also generally known as illite clays. Illite clays are similar in structure to smectite clays, but have their 2:1 layers bound together by poorly hydrated potassium ions, and for that reason do not swell.

In preferred aspects, a therapeutic clay of the present disclosure is a mixed-layer clay. Mixed-layer clays are generally referred to as rectorite and are composed of ordered mixed layers of illite and smectite. Layers of illite and smectite in rectorite clays may be random or regular. Ordering of illite and smectite layers in rectorite may be referred to as $R^0$ ordered or $R^1$ ordered illite-smectite. $R^1$-ordered illite-smectite is ordered in an ISISIS fashion, whereas $R^0$ describes random ordering. Other advanced ordering types may also be described. In some aspects, a clay of the present disclosure is a rectorite having $R^1$ ordered layers of illite and smectite.

A therapeutic clay of the present disclosure is a K-rectorite. More preferably, the therapeutic clay is a K-rectorite comprising therapeutic effective amounts of a reducing agent. Even more preferred, the therapeutic clay is a K-rectorite comprising therapeutic effective amounts of pyrite, or a K-rectorite comprising therapeutic effective amounts of $Fe^{3+}$.

A therapeutic clay of the present disclosure may be an unrefined naturally occurring therapeutic clay. Alternatively, the clay may be a refined clay purified from other material normally present in naturally occurring clay. Additionally, a clay may be purified to provide a substantially single form of the therapeutic clay. For instance, when the clay is a rectorite clay, the clay may be purified to provide a substantially pure K-rectorite clay, a substantially pure Na-rectorite clay, or a substantially pure Ca-rectorite clay. In some aspects, the clay is a naturally occurring therapeutic clay. In other aspects, the therapeutic clay is a refined clay. In other aspects, the therapeutic clay is a purified clay.

In some aspects, the therapeutic clay is an unrefined, naturally occurring therapeutic clay. In another aspect, the clay is a refined naturally occurring therapeutic clay. In yet other aspects, the clay is synthesized. Methods of synthesizing therapeutic clays may be as described in U.S. Patent Publication No. 2013/0004544, the disclosure of which is incorporated by reference herein in its entirety. In other aspects, therapeutic clays are naturally mined, and the levels of reducing agents in the mined clays are adjusted to provide therapeutic effective amounts of reducing agents in the clay.

In some aspects, the therapeutic clay of the present disclosure is a naturally mined clay from an open pit mine in hydrothermally altered, pyroclastic material in the Cascade Mountains. Without wishing to be bound by theory, the therapeutic properties of the clay may be due to a rare transition metal combination, including a level of pyrite ranging from about 3% to about 10% wt/wt and/or a level of pyrite ranging from about 1% to about 5% wt/wt.

In other aspects, the clay of the present disclosure is a natural red clay mined in the Cascade Mountain region of Oregon, more specifically a red clay mined in the crater lake region of the Cascade Mountains of Oregon. Without wishing to be bound by theory, the therapeutic properties of the red clay may be due to the presence of therapeutic effective amounts of aluminum as described above, among other properties.

The clay may also be modified with various substituents to alter the properties of the day. Non-limiting examples of modifications include modification with organic material, polymers, reducing agents, and various elements such as sodium, iron, silver, or bromide, or by treatment with a strong acid. In some aspects, a clay of the present disclosure is modified with reducing metal oxides. In some alternatives of the aspects, when the clay is modified with reducing metal oxides, the day is modified with pyrite.

The particle size of the clay may be an important factor that can influence its effectiveness, as well as bioavailability, blend uniformity, segregation, and flow properties. In general, smaller particle sizes of clay increase its effectiveness by increasing the surface area. In various aspects, the average particle size of the clay is less than about 500 microns in diameter, or less than about 450 microns in diameter, or less than about 400 microns in diameter, or less than about 350 microns in diameter, or less than about 300 microns in diameter, or less than about 250 microns in diameter, or less than about 200 microns in diameter, or less than about 150 microns in diameter, or less than about 100 microns in diameter, or less than about 75 microns in diameter, or less than about 50 microns in diameter, or less than about 25 microns in diameter, or less than about 15 microns in diameter. In some applications, the use of particles less than 15 microns in diameter may be advantageous. Preferably, the average particle size of the clay is about 1 to about 200 microns in diameter, preferably from about 10 to about 150 microns in diameter.

Similarly, in aspects wherein a reducing agent may be added to a clay, the particle size of a reducing agent may also be an important factor that can influence its effectiveness, and in general, smaller particle sizes increase its effectiveness. Preferably, the average particle size of the reducing agent that may be added to the clay is less than 1 micron in size.

B. Dietary Supplements or Feed Compositions Comprising a Therapeutic Clay

One aspect of the present invention provides dietary supplements or feed compositions comprising a therapeutically effective amount of a therapeutic clay. An effective amount of a therapeutic clay in a feed supplement composition can and will vary depending on the clay, the body weight, sex, age and/or medical condition of the animal, the severity and extent of the infectious disease in the animal, the method of administration, the duration of treatment, as well as the species of the animal, and may be determined experimentally using methods known in the art.

Generally, the amount of a therapeutic clay present in a feed or supplement composition will be at least 0.001% (w/w) of the total composition. In one aspect, the amount of clay in the composition ranges from about 0.001% to about 100% (w/w). For instance, the amount of clay in the composition may range from about 0.001% to about 50% (w/w), from about 25% to about 75% (w/w), or about 50% to about 100% (w/w). Preferably, the amount of clay in a feed or supplement composition ranges from between about 0.001% to about 15% (w/w), more preferably from about 0.1% to about 10% (w/w), and even more preferably from about 0.1% to about 0.5% (w/w).

The terms "feed", "food", "feed composition", and "feed supplement", are used herein interchangeably and may refer to any feed composition normally fed to an animal. Feed compositions normally fed to an animal are known in the art. A feed composition may include one or more components of an animal feed. Non-limiting examples of feed matter or animal feed matter may include, without limitation: corn or a component of corn, such as, for example, corn meal, corn fiber, corn hulls, corn DDGS (distiller's dried grain with solubles), silage, ground corn, corn germ, corn gluten, corn oil, or any other portion of a corn plant; soy or a component of soy, such as, for example, soy oil, soy meal, soy hulls, soy silage, ground soy, or any other portion of a soy plant, wheat or any component of wheat, such as, for example, wheat meal, wheat fiber, wheat hulls, wheat chaff, ground wheat, wheat germ, or any other portion of a wheat plant; canola, such as, for example, canola oil, canola meal, canola protein, canola hulls, ground canola, or any other portion of a canola plant; sunflower or a component of a sunflower plant; sorghum or a component of a sorghum plant; sugar beet or a component of a sugar beet plant; cane sugar or a component of a sugarcane plant; barley or a component of a barley plant; palm oil, palm kernel or a component of a palm plant; glycerol; corn steep liquor: a waste stream from an agricultural processing facility; lecithin; rumen protected fats: molasses; soy molasses: flax: peanuts; peas; oats; grasses, such as orchard grass and fescue; fish meal, meat & bone meal; feather meal: and poultry byproduct meal; and alfalfa and/or clover used for silage or hay, and various combinations of any of the feed ingredients set forth herein, or other feed ingredients generally known in the art. As it will be recognized in the art, a feed composition may further be supplemented with amino acids, vitamins, minerals, and other feed additives such as other types of enzymes, organic acids, essential oils, probiotics, prebiotics, antioxidants, pigments, anti-caking agents, and the like, as described further below.

A feed composition may be formulated for administration to any animal subject. Suitable subjects include all mammals, avian species, and aquaculture. Non-limiting examples of food animals include poultry (e.g., chickens, including broilers, layers, and breeders, ducks, game hens, geese, guinea fowl/hens, quail, and turkeys), beef cattle, dairy cattle, veal, pigs, goats, sheep, bison, and fishes. Suitable companion animals include, but are not limited to, cats, dogs, horses, rabbits, rodents (e.g., mice, rats, hamsters, gerbils, and guinea pigs), hedgehogs, and ferrets. Examples of research animals include rodents, cats, dogs, rabbits, pigs, and non-human primates. Non-limiting examples of suitable zoo animals include non-human primates, lions, tigers, bears, elephants, giraffes, and the like.

According to various aspects of the present invention, the feed may be in any suitable form known in the animal feed art, and may be a wet or dry component. For example, according to certain aspects, the feed composition may be in a form selected from the group consisting of a complete feed, a feed supplement, a feed additive, a premix, a topdress, a tub, a mineral, a meal, a block, a pellet, a mash, a liquid supplement, a drench, a bolus, a treat, and combinations of any thereof. Additionally, a feed sample may optionally be ground before preparing a feed composition.

The dietary supplements or feed compositions may optionally comprise at least one additional nutritive and/or pharmaceutical agent. For instance, the at least one additional nutritive and/or pharmaceutical agent may be selected from the group consisting of vitamin, mineral, amino acid, antioxidant, probiotic, essential fatty acid, and pharmaceutically acceptable excipient. The compositions may include one additional nutritive and/or pharmaceutical component or a combination of any of the foregoing additional components in varying amounts. Suitable examples of each additional component are detailed below.

a. Vitamins

Optionally, the dietary supplement of the invention may include one or more vitamins. Suitable vitamins for use in the dietary supplement include vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

The dietary supplement may include one or more forms of an effective amount of any of the vitamins described herein or otherwise known in the art. Non-limiting examples of vitamins include vitamin K, vitamin D, vitamin C, and biotin. An "effective amount" of a vitamin typically quantifies an amount at least about 10% of the United States Recommended Daily Allowance ("RDA") of that particular vitamin for a subject. It is contemplated, however, that amounts of certain vitamins exceeding the RDA may be beneficial for certain subjects. For example, the amount of a given vitamin may exceed the applicable RDA by 100%, 200%, 300%, 400%, 500% or more.

b. Minerals

In addition to the metal chelates or metal salts described in Section IA, the dietary supplement may include one or more minerals or mineral sources. Non-limiting examples of minerals include, without limitation, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In an aspect, the mineral may be a form of calcium. Suitable forms of calcium include calcium alpha-ketoglutarate, calcium acetate, calcium alginate, calcium ascorbate, calcium aspartate, calcium caprylate, calcium carbonate, calcium chelates, calcium chloride, calcium citrate, calcium citrate malate, calcium formate, calcium glubionate, calcium glucoheptonate, calcium gluconate, calcium glutarate, calcium glycerophosphate, calcium lactate, calcium lysinate, calcium malate, calcium orotate, calcium oxalate, calcium oxide, calcium pantothenate, calcium phosphate, calcium pyrophosphate, calcium succinate, calcium sulfate, calcium undecylenate, coral calcium, dicalcium citrate, dicalcium malate, dihydroxycalcium malate, dicalcium phosphate, and tricalcium phosphate.

Generally speaking, the dietary supplement may include one or more forms of an effective amount of any of the minerals described herein or otherwise known in the art. An "effective amount" of a mineral typically quantifies an amount at least about 10% of the United States Recommended Daily Allowance ("RDA") of that particular mineral for a subject. It is contemplated, however, that amounts of certain minerals exceeding the RDA may be beneficial for certain subjects. For example, the amount of a given mineral may exceed the applicable RDA by 100%, 200%, 300%, 400%, 500% or more. Typically, the amount of mineral included in the dietary supplement may range from about 1 mg to about 1500 mg, about 5 mg to about 500 mg, or from about 50 mg to about 500 mg per dosage.

c. Essential Fatty Acids

Optionally, the dietary supplement may include a source of an essential fatty acid. The essential fatty acid may be isolated or it may be an oil source or fat source that contains an essential fatty acid. In one aspect, the essential fatty acid may be a polyunsaturated fatty acid (PUFA), which has at least two carbon-carbon double bonds generally in the cis-configuration. The PUFA may be a long chain fatty acid having at least 18 carbons atoms. The PUFA may be an omega-3 fatty acid in which the first double bond occurs in the third carbon-carbon bond from the methyl end of the carbon chain (i.e., opposite the carboxyl acid group). Examples of omega-3 fatty acids include alpha-linolenic acid (18:3, ALA), stearidonic acid (18:4), eicosatetraenoic acid (20:4), eicosapentaenoic acid (20:5; EPA), docosatetraenoic acid (22:4), n-3 docosapentaenoic acid (22:5; n-3DPA), and docosahexaenoic acid (22:6; DHA). The PUFA may also be an omega-5 fatty acid, in which the first double bond occurs in the fifth carbon-carbon bond from the methyl end. Non-limiting examples of omega-5 fatty acids include myristoleic acid (14:1), myristoleic acid esters, and cetyl myristoleate. The PUFA may also be an omega-6 fatty acid, in which the first double bond occurs in the sixth carbon-carbon bond from the methyl end. Examples of omega-6 fatty acids include linoleic acid (18:2), gamma-linolenic acid (18:3), eicosadienoic acid (20:2), dihomo-gamma-linolenic acid (20:3), arachidonic acid (20:4), docosadienoic acid (22:2), adrenic acid (22:4), and n-6 docosapentaenoic acid (22:5). The fatty acid may also be an omega-9 fatty acid, such as oleic acid (18:1), eicosenoic acid (20:1), mead acid (20:3), erucic acid (22-1), and nervonic acid (24:1).

In another aspect, the essential fatty acid source may be a seafood-derived oil. The seafood may be a vertebrate fish or a marine organism, such that the oil may be fish oil or marine oil. The long chain (20C, 22C) omega-3 and omega-6 fatty acids are found in seafood. The ratio of omega-3 to omega-6 fatty acids in seafood ranges from about 8:1 to 20:1. Seafood from which oil rich in omega-3 fatty acids may be derived includes, but is not limited to, abalone scallops, albacore tuna, anchovies, catfish, clams, cod, gem fish, herring, lake trout, mackerel, menhaden, orange roughy, salmon, sardines, sea mullet, sea perch, shark, shrimp, squid, trout, and tuna.

In yet another aspect, the essential fatty acid source may be a plant-derived oil. Plant and vegetable oils are rich in omega-6 fatty acids. Some plant-derived oils, such as flaxseed oil, are especially rich in omega-3 fatty acids. Plant or vegetable oils are generally extracted from the seeds of a plant, but may also be extracted from other parts of the plant. Plant or vegetable oils that are commonly used for cooking or flavoring include, but are not limited to, acai oil, almond oil, amaranth oil, apricot seed oil, argan oil, avocado seed oil, babassu oil, ben oil, blackcurrant seed oil, Borneo tallow nut oil, borage seed oil, buffalo gourd oil, canola oil, carob pod oil, cashew oil, castor oil, coconut oil, coriander seed oil, corn oil, cottonseed oil, evening primrose oil, false flax oil, flax seed oil, grapeseed oil, hazelnut oil, hemp seed oil, kapok seed oil, lallemantia oil, linseed oil, macadamia oil, meadowfoam seed oil, mustard seed oil, okra seed oil, olive oil, palm oil, palm kernel oil, peanut oil, pecan oil, pequi oil, *perilla* seed oil, pine nut oil, pistachio oil, poppy seed oil, prune kernel oil, pumpkin seed oil, *quinoa* oil, ramtil oil, rice bran oil, safflower oil, sesame oil, soybean oil, sunflower oil, tea oil, thistle oil, walnut oil, or wheat germ oil. The plant-derived oil may also be hydrogenated or partially hydrogenated.

In still a further aspect, the essential fatty acid source may be an algae-derived oil. Commercially available algae-derived oils include those from *Crypthecodinium cohnii* and *Schizochytrium* sp. Other suitable species of algae, from which oil is extracted, include *Aphanizomenon flos-aquae, Bacilliarophy* sp., *Botryococcus braunii, Chlorophyceae* sp., *Dunaliella tertiolecta, Euglena gracilis, Isochrysis galbana, Nannochloropsis salina, Nannochloris* sp., *Neochloris oleoabundans, Phaeodactylum tricornutum, Pleurochrysis carterae, Prymnesium parvum, Scenedesmus dimorphus, Spirulina* sp., and *Tetraselmis chui*.

d. Amino Acids

The dietary supplement may optionally include from one to several amino acids. Suitable amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs. In certain aspects, the amino acid will be selected from the essential amino acids. An essential amino acid is generally described as one that cannot be synthesized de novo by the organism, and therefore, must be provided in the diet. By way of non-limiting example, the essential amino acids for humans include: L-histidine, L-isoleucine, L-leucine, L-lysine. L-methionine, L-phenylalanine, L-valine and L-threonine.

e. Antioxidants

The dietary supplement may include one or more suitable antioxidants. As will be appreciated by a skilled artisan, the suitability of a given antioxidant will vary depending upon the species to which the dietary supplement will be administered. Non-limiting examples of antioxidants include ascorbic acid and its salts, ascorbyl palmitate, ascorbyl stearate, anoxomer, N-acetylcysteine, benzyl isothiocyanate, o-, m- or p-amino benzoic acid (o is anthranilic acid, p is PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, p-coumaric acid, curcurin, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eugenol, ferulic acid, flavonoids, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinnamic acid, hydroxyglutaric acid, hydroquinone, N-hydroxysuccinic acid, hydroxytyrosol, hydroxyurea, lactic acid and its salts, lecithin, lecithin citrate; R-alpha-lipoic acid, lutein, lycopene, malic acid, maltol, 5-methoxy tryptamine, methyl gallate, monoglyceride citrate, monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, propyl gallate, polyphosphates, quercetin, trans-resveratrol, rosmarinic acid, sesamol, silymarin, sinapic acid, succinic acid, stearyl citrate, syringic acid, tartaric acid, thymol, tocopherols (i.e. alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, zeaxanthin, or combinations thereof.

Natural antioxidants that may be included in the dietary supplement include, but are not limited to, apple peel extract, blueberry extract, carrot juice powder, clove extract, coffeeberry, coffee bean extract, cranberry extract, *eucalyptus* extract, ginger powder, grape seed extract, green tea, olive leaf, parsley extract, peppermint, pimento extract, pomace, pomegranate extract, ice bran extract, rosehips, rosemary extract, sage extract, tart cherry extract, tomato extract, turmeric, and wheat germ oil.

f. Anti-Inflammatory Agents

The dietary supplement may optionally include at least one anti-inflammatory agent. In one aspect, the anti-inflammatory agent may be a synthetic non-steroidal anti-inflammatory drug (NSAID) such as acetylsalicylic acid, dichlophenac, indomethacin, oxamethacin, ibuprofen, indoprofen, naproxen, ketoprofen, mefamanic acid, metamizole, piroxicam, and celecoxib. In an alternate aspect, the anti-inflammatory agent may be a prohormone that modulates inflammatory processes. Suitable prohormones having this property include prohormone convertase 1, proopiomelanocortin, prohormone B-type natriuretic peptide, SMR1 prohormone, and the like. In another aspect, the anti-inflammatory agent may be an enzyme having anti-inflammatory effects. Examples of anti-inflammatory enzymes include bromelain, papain, serrapeptidase, and proteolytic enzymes such as pancreatin (a mixture of trypsin, amylase and lipase).

In still another aspect, the anti-inflammatory agent may be a peptide with anti-inflammatory effects. For example, the peptide may be an inhibitor of phospholipase A2, such as antiflammin-1, a peptide that corresponds to amino acid residues 246-254 of lipocortin; antiflammin-2, a peptide that corresponds to amino acid residues 39-47 of uteroglobin; S7 peptide, which inhibits the interaction between interleukin 6 and interleukin 6 receptor; RP1, a prenyl protein inhibitor; and similar peptides. Alternatively, the anti-inflammatory peptide may be cortistatin, a cyclic neuropeptide related to somatostatin, or peptides that correspond to an N-terminal fragment of SV-IV protein, a conserved region of E-, L-, and P-selectins, and the like. Other suitable anti-inflammatory preparations include collagen hydrolysates and milk micronutrient concentrates (e.g., MicroLactin® available from Stolle Milk Biologics, Inc., Cincinnati, OH), as well as milk protein hydrolysates, casein hydrolysates, whey protein hydrolysates, and plant protein hydrolysates.

In a further aspect, the anti-inflammatory agent may be a probiotic that has been shown to modulate inflammation. Suitable immunomodulatory probiotics include lactic acid bacteria such as acidophilli, lactobacilli, and bifidophilli. In yet another aspect, the anti-inflammatory agent may be a plant extract having anti-inflammatory properties. Non-limiting examples of suitable plant extracts with anti-inflammatory benefits include blueberries, boswella, black *catechu* and Chinese skullcap, celery seed, chamomile, cherries, devils claw, *eucalyptus*, evening primrose, ginger, hawthorne berries, horsetail, *Kalopanax pictus* bark, licorice root, turmeric, white wallow, willow bark, and *yucca*.

g. Probiotics

Probiotics and prebiotics may include yeast and bacteria that help establish an immune protective rumen or gut microflora as well as small oligosaccharides. By way of non-limiting example, yeast-derived probiotics and prebiotics include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In one aspect, the yeast-derived agent may be β-glucans and/or mannanoligosaccharides. Sources for yeast cell wall derived components include *Saccharomyces bisporus, Saccharomyces boulardii, Saccharomyces cerevisiae, Saccharomyces capsularis. Saccharomyces delbrueckii, Saccharomyces fermentati, Saccharomyces lugwigii, Saccharomyces microellipsoides, Saccharomyces pastorianus. Saccharomyces rosei, Candida albicans, Candida cloaceae, Candida tropicalis, Candida utilis, Geotrichum candidum, Hansenula americana, Hansenula anomala, Hansenula wingei,* and *Aspergillus oryzae.*

Probiotics and prebiotics may also include bacteria cell wall derived agents such as peptidoglycan and other components derived from gram-positive bacteria with a high content of peptidoglycan. Exemplary gram-positive bacteria include *Lactobacillus acidophilus, Bifedobact thermophilum, Bifedobat longhum, Streptococcus faecium, Bacillus pumilus, Bacillus subtilis. Bacillus licheniformis, Lactobacillus acidophilus, Lactobacillus casei, Enterococcus faecium, Bifidobacterium bifidium, Propionibacterium acidipropionici, Propionibacteriium freudenreichii,* and *Bifidobacterium pseudolongum.* h. Herbals

Suitable herbals and herbal derivatives, as used herein, refer to herbal extracts, and substances derived from plants and plant parts, such as leaves, flowers and roots, without limitation. Non-limiting exemplary herbals and herbal derivatives include agrimony, alfalfa, aloe vera, amaranth, *angelica*, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, phytogenic, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, *echinacea*, elecampane, ephedra, *eucalyptus*, evening primrose, eyebright, false unicorn, fennel, fenugreek, figwort, flaxseed, garlic, gentian, ginger, *ginseng*, golden seal, gotu kola, gum weed, hawthorn, hops, horehound, horseradish, horsetail, hoshouwu, *hydrangea*, hyssop, iceland moss, irish moss, jojoba, juniper, kelp, lady's slipper, lemon grass, licorice, *lobelia*, mandrake, marigold, marjoram, marshmallow, mistletoe, mullein, mustard, myrrh, nettle, oatstraw, oregon grape, *papaya*, parsley, passion flower, peach, pennyroyal, peppermint, periwinkle, plantain, pleurisy root, pokeweed, prickly ash, *psyllium*, quassia, queen of the meadow, red clover, red raspberry, redmond clay, rhubarb, rose hips, rosemary, rue, safflower, saffron, sage, St. John's wort, sarsaparilla, *sassafras*, saw palmetto, skullcap, senega, *senna*, shepherd's purse, slippery elm, spearmint, spikenard, squawvine, stillingia, strawberry, taheebo, thyme, *Uva ursi*, valerian, violet, watercress, white oak bark, white pine bark, wild cherry, wild lettuce, wild yam, willow, wintergreen, witch hazel, wood betony, wormwood, yarrow, yellow dock, yerba santa, *yucca* and combinations thereof.

i. Pigments

Suitable non-limiting pigments include actinioerythrin, alizarin, alloxanthin, β-apo-2'-carotenal, apo-2-lycopenal, apo-6'-lycopenal, astacein, astaxanthin, azafrinaldehyde, aacterioruberin, aixin, α-carotine, β-carotine, γ-carotine, β-carotenone, canthaxanthin, capsanthin, capsorubin, citranaxanthin, citroxanthin, crocetin, crocetinsemialdehyde, crocin, crustaxanthin, cryptocapsin, α-cryptoxanthin, β-cryptoxanthin, cryptomonaxanthin, cynthiaxanthin, decaprenoxanthin, dehydroadonirubin, diadinoxanthin, 1,4-diamino-2,3-dihydroanthraquinone, 1,4-dihydroxyanthraquinone, 2,2'-Diketospirilloxanthin, eschscholtzxanthin, eschscholtzxanthone, flexixanthin, foliachrome, fucoxanthin, gazaniaxanthin, hexahydrolycopene, hopkinsiaxanthin, hydroxyspheriodenone, isofucoxanthin, loroxanthin, lutein, luteoxanthin, lycopene, lycopersene, lycoxanthin, morindone, mutatoxanthin, neochrome, neoxanthin, nonaprenoxanthin, OH-Chlorobactene, okenone, oscillaxanthin, paracentrone, pectenolone, pectenoxanthin, peridinin, phleixanthophyll, phoeniconone, phoenicopterone, phoenicoxanthin, physalien, phytofluene, pyrrhoxanthininol, quinones, rhodopin, rhodopinal, rhodopinol, rhodovibrin, rhodoxanthin, rubixanthone, saproxanthin, semi-α-carotenone, semi-β-carotenone, sintaxanthin, siphonaxanthin, siphonein, spheroidene, tangeraxanthin, torularhodin, torularhodin methyl ester, torularhodinaldehyde, torulene, 1,2,4-trihydroxyanthraquinone, triphasiaxanthin, trollichrome, vaucheriaxanthin, violaxanthin, wamingone, xanthin, zeaxanthin, α-zeacarotene and combinations thereof.

j. Pharmaceutical Agents

Suitable non-limiting pharmaceutically acceptable agents include an acid/alkaline-labile drug, a pH dependent drug, or a drug that is a weak acid or a weak base. Examples of acid-labile drugs include statins (e.g., pravastatin, fluvastatin and atorvastatin), antibiotics (e.g., penicillin G, ampicillin, streptomycin, erythromycin, clanthromycin and azithromycin), nucleoside analogs (e.g., dideoxyinosine (ddI or didanosine), dideoxyadenosine (ddA), dideoxycytosine (ddC)), salicylates (e.g., aspirin), digoxin, bupropion, pancreatin, midazolam, and methadone. Drugs that are only soluble at acid pH include nifedipine, emonapride, nicardipine, amosulalol, noscapine, propafenone, quinine, dipyridamole, josamycin, dilevalol, labetalol, enisoprost, and metronidazole. Drugs that are weak acids include phenobarbital, phenytoin, zidovudine (AZT), salicylates (e.g., aspirin), propionic acid compounds (e.g., ibuprofen), indole derivatives (e.g., indomethacin), fenamate compounds (e.g., meclofenamic acid), pyrroleakanoic acid compounds (e.g., tolmetin), cephalosporns (e.g., cephalothin, cephalaxin, cefazolin, cephradine, cephapirin, cefamandole, and cefoxitin), 6-fluoroquinolones and prostaglandins. Drugs that are weak bases include adrenergic agents (e.g., ephedrine, desoxyephedrine, phenylephrine, epinephrine, salbutamol, and terbutaline), cholinergic agents (e.g., physostigmine and neostigmine), antispasmodic agents (e.g., atropine, methantheline, and papaverine), curariform agents (e.g., chlorisondamine), tranquilizers and muscle relaxants (e.g., fluphenazine, thioridazine, trifluoperazine, chlorpromazine, and triflupromazine), antidepressants (e.g., amitriptyline and nortriptyline), antihistamines (e.g., diphenhydramine, chlorpheniramine, dimenhydrinate, tripelennamine, perphenazine, chlorprophenazine, and chlorprophenpyridamine), cardioactive agents (e.g., verapamil, diltiazem, gallapomil, cinnarizine, propranolol, metoprolol and nadolol), antimalarials (e.g., chloroquine), analgesics (e.g., propoxyphene and meperidine), antifungal agents (e.g., ketoconazole and itraconazole), antimicrobial agents (e.g., cefpodoxime, proxetil, and enoxacin), caffeine, theophylline, and morphine. In another aspect, the drug may be a biphosphonate or another drug used to treat osteoporosis. Non-limiting examples of a biphosphonate include alendronate, ibandronate, risedronate, zoledronate, pamidronate, neridronate, olpadronate, etidronate, clodronate, and tiludronate. Other suitable drugs include estrogen, selective estrogen receptor modulators (SERMs), and parathyroid hormone (PTH) drugs. In yet another aspect, the drug may be an antibacterial agent (antibiotic). Suitable antibiotics include aminoglycosides (e.g., amikacin, gentamicin, kanamycin, neomycin, netilmicin, streptomycin, and tobramycin), carbecephems (e.g.: loracarbef), a carbapenem (e.g., certapenem, imipenem, and meropenem), cephalosporins (e.g., cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone), macrolides (e.g., azithromycin, clarithromycin, dirithromycin, erythromycin, and troleandomycin), monobactam, penicillins (e.g., amoxicillin, ampicillin, carbenicillin, cloxacillin, dicloxacillin, nafcillin, oxacillin, penicillin G, penicillin V, piperacillin, and ticarcillin), polypeptides (e.g., bacitracin, colistin, and polymyxin B), quinolones (e.g., ciprofloxacin, enoxacin, gatifloxacin, levofloxacin, lomefloxacin, moxifloxacin, norfloxacin, ofloxacin, and trovafloxacin), sulfonamides (e.g., mafenide, sulfacetamide, sulfamethizole, sulfasalazine, sulfisoxazole, and trimethoprim-sulfamethoxazole), and tetracyclines (e.g., demeclocycline, doxycycline, minocycline, and oxytetracycline). In an alternate aspect, the drug may be an antiviral protease inhibitor (e.g., amprenavir, fosamprenavir, indinavir, lopinavir/ritonavir, ritonavir, saquinavir, and nelfinavir). In still another aspect, the drug may be a cardiovascular drug. Examples of suitable cardiovascular agents include cardiotonic agents (e.g., *digitalis* (digoxin), ubidecarenone, and dopamine), vasodilating agents (e.g., nitroglycerin, captopril, dihydralazine, diltiazem, and isosorbide dinitrate), antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril), beta blockers (e.g., levobunolol, pindolol, timolol maleate, bisoprolol, carvedilol, and butoxamine), alpha blockers (e.g., doxazosin, prazosin, phenoxybenzamine, phentolamine, tamsulosin, alfuzosin, and terazosin), calcium channel blockers (e.g., amlodipine, felodipine, nicardipine, nifedipine, nimodipine, nisoldipine, nitrendipine, lacidipine, lercanidipine, verapamil, gallapomil, and diltiazem), and anticlot agents (e.g., dipyrimadole).

k. Excipients

A variety of commonly used excipients in dietary supplement formulations may be selected on the basis of compatibility with the active ingredients. Non-limiting examples of suitable excipients include an agent selected from the group consisting of non-effervescent disintegrants, a coloring agent, a flavor-modifying agent, an oral dispersing agent, a stabilizer, a preservative, a diluent, a compaction agent, a lubricant, a filler, a binder, taste-masking agents, an effervescent disintegration agent, and combinations of any of these agents.

In one aspect, the excipient is a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof. The polypeptide may be any arrangement of amino acids ranging from about 100 to about 300,000 daltons.

In another aspect, the excipient may be a filler. Suitable fillers include carbohydrates, inorganic compounds, and polyvinylpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may comprise a non-effervescent disintegrant. Suitable examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In another aspect, the excipient may be an effervescent disintegrant. By way of non-limiting example, suitable effervescent disintegrants include sodium bicarbonate in combination with citric acid and sodium bicarbonate in combination with tartaric acid.

The excipient may comprise a preservative. Suitable examples of preservatives include antioxidants, such as a-tocopherol or ascorbate, and antimicrobials, such as parabens, chlorobutanol or phenol.

In another aspect, the excipient may include a diluent. Diluents suitable for use include pharmaceutically acceptable saccharide such as sucrose, dextrose, lactose, microcrystalline cellulose, fructose, xylitol, and sorbitol; polyhydric alcohols; a starch; pre-manufactured direct compression diluents; and mixtures of any of the foregoing.

The excipient may include flavors. Flavors incorporated into the outer layer may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, *eucalyptus*, vanilla, citrus oil, such as lemon oil, orange oil, grape and grapefruit oil, fruit essences including apple, peach, pear, strawberry, raspberry, cherry, plum, pineapple, and apricot.

In another aspect, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia rebaudiana* (Stevioside); chloro derivatives of sucrose such as sucralose; sugar alcohols such as sorbitol, mannitol, sylitol, and the like.

In another aspect, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

Depending upon the aspect, it may be desirable to provide a coloring agent in the outer layer. Suitable color additives include food, drug and cosmetic colors (FD&C), drug and cosmetic colors (D&C), or external drug and cosmetic colors (Ext D&C). These colors or dyes, along with their corresponding lakes, and certain natural and derived colorants, may be suitable for use in the present invention depending on the aspect.

The excipient may include a taste-masking agent. Taste-masking materials include, e.g., cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Sepifilm-LC, Pharmacoat®, Metolose SR, Opadry YS, PrimaFlo, MP3295A, Benecel MP824, and Benecel MP843; methylcellulose polymers such as Methocel® and Metolose®; Ethylcelluloses (EC) and mixtures thereof such as E461, Ethocel®, Aqualon&-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol co-polymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials. In other aspects, additional taste-masking materials contemplated are those described in U.S. Pat. Nos. 4,851,226, 5,075,114, and 5,876,759, each of which is hereby incorporated by reference in its entirety.

In various aspects, the excipient may include a pH modifier. In certain aspects, the pH modifier may include sodium carbonate or sodium bicarbonate.

The dietary supplement or feed compositions detailed herein may be manufactured in one or several dosage forms. In one aspect, the dosage form will be an oral dosage form. Suitable oral dosage forms may include a tablet, for example a suspension tablet, a chewable tablet, an effervescent tablet or caplet; a pill; a powder, such as a sterile packaged powder, a dispensable powder, and an effervescent powder, a capsule including both soft or hard gelatin capsules or non-animal derived polymers, such as hydroxypropyl methylcellulose capsules (i.e., HPMC) or pullulan; a lozenge; a sachet; a sprinkle, a reconstitutable powder or shake; a troche; pellets; granules; liquids; lick blocks, suspensions; emulsions; or semisolids and gels. Alternatively, the dietary supplement may be incorporated into a food product or powder for mixing with a liquid, or administered orally after only mixing with a non-foodstuff liquid. As will be appreciated by a skilled artisan, the dietary supplements, in addition to being suitable for administration in multiple dosage forms, may also be administered with various dosage regimens. Additionally, the therapeutic clay may simply be added to any dosage form of a dietary supplement or feed composition.

The amount and types of ingredients (i.e., metal chelate, chondroprotective agents, vitamin, mineral, amino acid, antioxidant, yeast culture, and essential fatty acid), and other excipients useful in each of these dosage forms, are described throughout the specification and examples. It should be recognized that where a combination of ingredients and/or excipient, including specific amounts of these components, is described with one dosage form that the same combination could be used for any other suitable dosage form. Moreover, it should be understood that one of skill in the art would, with the teachings found within this application, be able to make any of the dosage forms listed above by combining the amounts and types of ingredients administered as a combination in a single dosage form or separate dosage forms and administered together as described in the different sections of the specification.

The dietary supplements of the present invention can be manufactured by conventional pharmacological techniques. Conventional pharmacological techniques include, e.g., one or a combination of methods: (1) dry mixing; (2) direct compression; (3) milling; (4) dry or non-aqueous granulation; (5) wet granulation: or (6) fusion. See, e.g., Lachman et al., The Theory and Practice of Industrial Pharmacy (1986). Other methods include, e.g., prilling, spray drying, pan coating, melt granulation, granulation, wurster coating, tangential coating, top spraying, extruding, coacervation and the like.

II. Methods of Using

Another aspect of the present disclosure provides methods of orally administering to the animal an effective amount of a therapeutic clay. An effective amount of the therapeutic clay is any amount of the clay that, when administered to an animal, will improve the performance of the animal when compared to the performance of an animal fed a control diet without the clay. The clay or any combination of the day with other ingredients can be used for oral administration.

Any method of oral administration can be used, provided the method is a controlled method of administration capable of administering an accurate amount of clay to the animal. For instance, the clay can be administered by sprinkling an accurate amount of clay over a feed composition (topping off) or by adding to drinking water to administer the accurate amount of clay upon ingestion of the feed or water by the animal. Alternatively, the clay can be formulated with a feed composition to administer the accurate amount of clay upon ingestion of the feed composition by the animal.

An animal can include, without limitation, companion animals such as cats, dogs, rabbits, horses, and rodents such as gerbils: agricultural animals such as cows, dairy cows, dairy calves, beef cattle, pigs, goats, sheep, horses, deer; zoo animals such as primates, elephants, zebras, large cats, bears, and the like; research animals such as rabbits, sheep, pigs, dogs, primates, mice, rats and other rodents; avians, including but not limited to chickens, ducks, turkeys, ostrich, and emu; and aquatic animals chosen from fish and crustaceans including, but not limited to, salmon, shrimp, carp, tilapia, and shell fish.

In some aspects, the animal is a livestock animal. The term "livestock" as used herein refers to domesticated animals raised in an agricultural setting to produce labor and commodities such as meat, eggs, milk, fur, leather, and wool. The term "livestock" can be used to refer solely to animals that are bred for consumption. The term can also be used to refer only to farmed mammalian animals, such as cattle, sheep, horses, pigs, and goats. In some aspects, the animal is a pig.

The method orally administers an effective amount of a therapeutic clay to the animal. As used herein, the phrase "effective amount" is used to mean an amount that is intended to qualify the amount of an agent or compound, that when administered, it will achieve the goal of improving the performance of an animal compared to the performance of the animal fed a control diet without the agent or compound.

The timing and duration of administration of the clay of the invention to an animal can and will vary. For instance, a clay can be administered routinely throughout the period when the animal is raised. A clay can be administered at various intervals. For instance, a clay can be administered daily, weekly, monthly or over a number of months In some aspects, a clay is administered daily. In other aspects, a clay is administered weekly. In yet other aspects, a clay is administered monthly. A clay can also be administered every three to six months. As it will be recognized in the art, the duration of treatment can and will vary and can be determined experimentally.

The clay can be administered to the animal in a single dose or a number of doses throughout the period of administration. For instance, a single dose of the clay can be administered after breeding, once during gestation, at birth, or once after farrowing. Alternatively, multiple doses of the clay can be administered during gestation, during lactation, and combinations thereof. For instance, administration of the clay can start after mating and continue to the end of lactation. In some aspects, the clay is administered from breeding until farrowing. For instance, when the animal is a pig, a clay can be administered three weeks prior to farrowing, or at day 110, 111, 112, 113, or 114 of gestation. In some aspects, the clay is administered from farrowing until weaning. The clay can also be administered throughout the period of lactation. In some aspects, the clay is administered throughout the periods of gestation and lactation.

In some aspects, the clay is administered orally to an animal by adding the clay to a feed, formulating the clay with the feed, or supplement formulation and feeding the feed or supplement formulation to the animal. Formulating the clay with a feed can be as described in Section B above.

When administered to an animal with a feed or supplement formulation, the amount of clay in the feed composition can range from about 0.1 lb/ton to 10 about lb/ton. For instance, the amount of clay in a feed composition can range from about 0.5 lb/ton to about 2.0 lb/ton. Alternatively, the amount of day in a feed composition can range from about 0.4 lb/ton to about 0.6 lb/ton. The amount of clay in a gestation feed composition can range from about 0.5 lb/ton to about 6.0 lb/ton. In some aspects, the amount of clay in a gestation feed composition ranges from about 0.5 lb/ton to about 4.0 lb/ton. The amount of clay in a lactation feed composition can range from about 0.5 lb/ton to about 6 lb/ton. In some aspects, the amount of clay in a lactation feed composition ranges from about 1 lb/ton to about 2 lb/ton.

As will be appreciated by one of skill in the art, a dose of a composition of the invention can and will vary depending on the animal, the frequency and timing of administration of the dose, body weight, sex, age and/or medical condition of the animal, the desired growth rate and efficiency, the method of administration, and the duration of treatment The rate of administration of the clay of the disclosure may depend on the level of reducing agent in the clay. For instance, the level of reducing agent in the clay may be determined before administration to adjust the level of clay that may be used. The oxidation-reduction potential of the clay can be determined and the level of clay used in a method, composition, or formulation of the present disclosure is adjusted based on the oxidation-reduction potential of the clay. The oxidation-reduction potential of the clay can provide a general measure of the therapeutic potential of a clay that may be used irrespective of the reducing agents present in the clay. Alternatively, the content of one or more specific reducing agents in the clay may be determined.

In some aspects, the amount of clay administered to a maternal animal can range from about 1.0 g/d to about 10 g/d, from about 0.1 g/d to about 8 g/d, from about 0.5 g/d to about 3 g/d, or from about 4.0 g/d to about 7 g/d. In some aspects, the amount of clay administered to a maternal animal ranges from about 0.1 g/d to about 5 g/d. The clay can be administered to an animal during gestation at a rate ranging from about 0.5 g/d to about 3 g/d. Alternatively, the clay can be administered to an animal during lactation at a rate ranging from about 4.0 g/d to about 5 g/d. Further, when the animal is a pig, the clay can be administered starting on about the $1^{st}$ day to about the $100^{th}$ of gestation.

Administering a therapeutically effective amount of the clay improves reproductive performance and litter performance in an animal. As used herein, the term "reproductive performance" refers to any aspect of animal health and wellbeing that could measurably affect reproduction of the animal. For instance, reproductive performance can be measured by the health and vitality of the animal, thereby making the animal more fit for reproduction and for producing healthy animals, the number of progeny produced by the animal, and the general health and vitality of the progeny produced by the animal. For instance, when a clay is administered to a sow, the number of pigs born at a weight of less than 1.7 lbs can be significantly reduced.

As used herein, the term "litter performance" refers to any aspect of health and wellbeing of a litter of the mother administered the clay that could measurably affect reproduction of the animal. It should be noted that when referring to litter performance after weaning, the improvement in performance is a result of the administration of the clay to the mother. As such, the litter of an animal administered the clay will have improved performance after weaning when the animal is not administered the clay.

In some aspects, administration of a therapeutically effective amount of the clay improves reproductive performance. Improving reproductive performance can comprise reducing embryonic loss, promoting pregnancy, increasing litter size, increasing the number of live births, improving the immune status of the maternal animal, reducing the concentration of fecal amino acids, reducing the concentration of fecal short-chained amino acid, and increasing litter birth weight.

Improving the immune status of the maternal animal can comprise an increased level of IFNγ and TNF-α in the maternal animal, and decreased levels of tumor necrosis factor related apoptosis inducing ligand (TRAIL) in the maternal animal. In some aspects, the level of pre-farrowing TNF-α in the maternal animal is positively correlated with total wean, negatively correlated with subsequent stillborns, and positively correlated with subsequent mummies. In some aspects, the level of pre-farrowing TRAIL is negatively correlated with subsequent total born and subsequent born alive. In some aspects, the level of wean IFN-γ is positively correlated with total wean.

In some aspects, administration of a therapeutically effective amount of the clay improves liter performance. Improving litter performance can comprise increasing the amount of young animal colostrum intake, reducing young animal pre-weaning mortality, reducing the number of young animals lost due to low viability, reducing the number of weaned young animals, improving the immune status of young animals at weaning, reducing the number of lightweight young animals from nursery to market, increasing the number of young animals marketed per sow, and increasing calculated litter weight gain. The immune status can comprise total immunoglobulins in blood.

A. Improving Performance in a Pig.

Another aspect of the disclosure encompasses a method of increasing the amount of piglet colostrum intake, reducing pre-weaning mortality, reducing the number of piglets lost due to low viability, reducing the number of weaned pigs, reducing the number of lightweight pigs from nursery to market, increasing the number of pigs marketed per sow, and increasing calculated litter weight gain. The method comprises orally administering to a sow an effective amount of a therapeutic clay. In some aspects, the sow is parity 2 or parity 6 or more.

The clay can be as described in Section I(A), and the clay formulations can be as described in Section I(B) above.

The clay can be administered during gestation, during lactation, and combinations thereof. For instance, the clay can be administered for a period of time during gestation. In some aspects, the clay is administered from breeding until farrowing. The clay can also be administered for a period of time during lactation. For instance, the clay can be administered from farrowing until weaning. In some aspects, the clay is administered starting on day 3 to day 93 of gestation.

In some aspects, the amount of clay in a feed composition can range from about 0.1 lb/ton to 10 lb/ton. For instance, the amount of clay in a gestation feed composition can range from about 0.1 lb/ton to 4.0 lb/ton. The amount of clay in a lactation feed composition can range from about 1.0 lb/ton to 2.0 lb/ton.

The amount of clay administered to a sow can range from about 1.0 g/d to about 10 g/d, from about 0.1 g/d to about 8 g/d, from about 0.5 g/d to about 3 g/d, or from about 4.0 g/d to about 7 g/d. Further, the clay can be administered starting three weeks after breeding, or on day 3 to 93 of gestation.

An additional aspect of the disclosure encompasses method of reducing embryonic loss, increasing litter size, increasing the number of live births, improving the immune status of the sow, reducing the concentration of sow fecal amino acids, reducing the concentration of maternal fecal short-chained amino acid, and increasing litter birth weight. The method comprises orally administering to a sow an effective amount of a therapeutic clay. In some aspects, the sow is parity 2 or parity 6 or more.

Yet another aspect of the disclosure encompasses a method of enhancing pig litter performance. The method comprises orally administering an effective amount of a therapeutic clay to a sow. In some aspects, the sow is parity 2, or parity 6 or more. Enhancing litter performance can comprise increasing the amount of piglet colostrum intake, reducing pre-weaning mortality, reducing the number of piglets lost due to low viability, reducing the number of weaned pigs, improving the immune status of piglets at weaning, reducing the number of lightweight piglets from nursery to market, increasing the number of pigs marketed per sow, and increasing calculated litter weight gain.

One aspect of the present disclosure encompasses a method of improving pig litter performance, the method comprising orally administering an effective amount of a therapeutic clay to a sow. Improving litter performance can comprise increasing amount of piglet colostrum intake, reducing piglet pre-weaning mortality, reducing the number of piglets lost due to low viability, reducing the number of weaned piglets, improving the immune status of piglets at weaning, reducing the number of lightweight young animals from nursery to market, increasing the number of piglets marketed per sow, and increasing calculated litter weight gain.

Definitions

When introducing elements of the present disclosure, the articles "a," "an," "the," and "said" are intended to mean that there are one or more of the elements. The use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities, and plural terms shall include the singular.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges can independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, "administering" is used in its broadest sense to mean contacting a subject with a composition disclosed herein, provided the method is a controlled method of administration capable of administering an accurate amount of clay to the animal.

The phrase "effective amount" is used to mean an amount that is intended to qualify the amount of an agent or compound, that when administered, it will achieve the goal of improving the performance of an animal compared to the performance of the animal fed a control diet without the agent or compound.

As used herein, the term "w/w" designates the phrase "by weight" and is used to describe the concentration of a particular substance in a mixture or solution.

As used herein, the term "subject" refers to a vertebrate species such as mammals, birds, reptiles, amphibians, and fish. The vertebrate species may be an embryo, a juvenile, or an adult. Examples of suitable mammals include, without limit, rodents, companion or domestic animals, livestock, and primates. Non-limiting examples of rodents include mice, rats, hamsters, gerbils, and guinea pigs. Non-limiting examples of livestock include goats, sheep, swine, cattle, llamas, and alpacas. Suitable primates include, but are not limited to, humans, capuchin monkeys, chimpanzees, lemurs, macaques, marmosets, tamarins, spider monkeys, squirrel monkeys, and vervet monkeys. Non-limiting examples of birds include chickens, turkeys, ducks, and geese.

As used herein, the terms "companion animal" or "domestic animal" refer to an animal typically kept as a pet for keeping in the vicinity of a home or domestic environment for company or protection, regardless of whether the animal is kept indoors or outdoors Non-limiting examples of companion animals or domestic animals include, but are not limited to, dogs, cats, house rabbits, ferrets, and horses.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. "Purify" or "purification" in other aspects means removing at least one contaminant from the composition to be purified. In this sense, purification does not require that the purified compound be homogenous, e.g., 100% pure.

As various changes could be made in the above-described cells and methods without departing from the scope of the invention, it is intended that all matter contained in the above description and in the examples given below, shall be interpreted as illustrative and not in a limiting sense.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1: Relationship Between Pro-Inflammatory Cytokines and Litter Size

Thirty-five sows (17 fed a control diet and 18 fed a diet containing clay) were used to determine the effect feeding clay has pro-inflammatory cytokines. Blood samples were taken on day 113 of gestation and again on day 18-19 of lactation. Serum samples were analyzed to determine the circulating levels of tumor necrosis factor alpha (TNF-$\alpha$), interferon gamma (INF-Y), and tumor necrosis factor related apoptosis inducing ligand (TRAIL). Sow reproductive measures and litter size were collected from the litter immediately following treatment with clay in the diet and from the subsequent litter following the treatment litter.

The data was transformed prior to analyses, as the serum cytokine levels were not normally distributed. Box-Cox transformations were used on the serum cytokine data to create a normal distribution. The data was then analyzed to determine mean differences and correlation analyses was conducted to relate the serum cytokine levels to sow performance data.

| Parameter | Transformation |
| --- | --- |
| Pre-farrow IFN-$\gamma$ | ^(0.25) |
| Pre-farrow TNF-$\alpha$ | ^(−0.25) |
| Pre-farrow TRAIL | ^(−0.25) |
| Wean IFN-$\gamma$ | ^(0.25) |
| Wean TNF-$\alpha$ | ^(−0.25) |
| Wean TRAIL | ^(−0.50) |

Sows fed a diet including clay had increased total born, born alive, and number of pigs weaned for performance immediately following consumption of the clay-based diet (Table 1). Additionally, subsequent total born and born alive was increased for sows fed a clay-based diet compared to sows fed the control diet. Serum IFNY increased and TRAIL decreased for sows fed the clay-based diet compared to sows fed a control diet, suggesting that feeding the clay to sows had a positive effect on controlling inflammation and that resulting litter size was increased.

Correlation analyses suggests that increased IFN$\gamma$ and decreased TRAIL were associated with increased litter size and reduced mummies in both the immediate and subsequent litter (Table 2). Pre-farrowing TNF-$\alpha$ was positively correlated with total wean (P=0.0838), negatively correlated with subsequent stillborns (P=0.0789), and positively correlated with subsequent mummies (P=0.0356). Pre-farrow TRAIL was negatively correlated with subsequent total born (P=0.0062) and born alive (P=0.0062). Wean IFN-$\gamma$ was positively correlated with total wean (P=0.0779). Wean TNF-$\alpha$ was negatively correlated with subsequent stillborns (P=0.0482), and positively correlated with subsequent mummies (P=0.0141). Wean TRAIL was negatively correlated with subsequent born alive (P=0.1067).

TABLE 1

ANOVA analysis to evaluate the differences between sows fed a control or a diet including clay during gestation and lactation

| Item | Control | therapeutic clay | SE | P-value | % change |
| --- | --- | --- | --- | --- | --- |
| # of sows | 17 | 18 | | | |
| Current parity | 4.2 | 4.0 | 0.4 | 0.76 | |
| Total born | 16.0 | 16.5 | 0.8 | 0.66 | +3.1 |
| Born alive | 14.7 | 15.3 | 0.7 | 0.57 | +4.1 |
| Stillborns, % | 3.7 | 4.8 | 1.2 | 0.52 | +29.7 |
| Mummies, % | 3.4 | 2.0 | 1.2 | 0.40 | −41.2 |
| Total wean | 13.0 | 14.0 | 0.6 | 0.21 | +7.7 |
| Subsequent parity | 5.2 | 5.0 | 0.4 | 0.76 | |
| Total born | 16.9 | 17.3 | 0.9 | 0.76 | +2.4 |
| Born alive | 14.0 | 14.1 | 1.1 | 0.96 | +0.7 |
| Stillborns, % | 11.7 | 10.5 | 3.3 | 0.79 | −10.3 |
| Mummies, % | 1.1 | 1.4 | 0.5 | 0.69 | +27.3 |

TABLE 1-continued

ANOVA analysis to evaluate the differences between sows fed a control or a diet including clay during gestation and lactation

| Item | Control | therapeutic clay | SE | P-value | % change |
|---|---|---|---|---|---|
| Sow biomarker Pre-farrow | | | | | |
| IFN-γ, pg/mL | 4,099 | 5,630 | 1,753 | 0.41 | +37.4 |
| TNF-α, pg/mL | 640 | 737 | 139 | 0.44 | +15.2 |
| TRAIL, pg/mL | 56.3 | 48.8 | 62.6 | 0.76 | −13.3 |
| At weaning | | | | | |
| IFN-γ, pg/mL | 2,356 | 3,695 | 2,384 | 0.41 | +56.8 |
| TNF-α, pg/mL | 449 | 488 | 109 | 0.70 | +8.7 |
| TRAIL, pg/ml | 39.8 | 31.3 | 240.5 | 0.51 | −21.4 |

TABLE 3

Dietary treatments and assigned colors for sows.

| Treatment | Additive | Inclusion Rate | Daily scoop size in gestation[1] | Daily scoop size in lactation[2] | No. of sows |
|---|---|---|---|---|---|
| 1. Control | None | None | — | — | 120 |
| 2. Clay | Therapeutic clay[4] | 2.0 lb/ton | ½ tsp[3] | 1 tsp[3] | 120 |
| | | Total | | | 480 |

[1] Calculated based on the assumption that the average feed intake is 5.0 lb/day in gestation.
[2] Calculated based on the assumption that the average feed intake is 10.0 lb/day in lactation.
[3] Scoop amounts equated 2.26 g/d and 4.52 g/d for gestation and lactation, respectively.
[4] 2 lb version (rather than 4 lb version) of therapeutic clay used for the study.

TABLE 2

Correlation analysis to evaluate the linear relationship between sow reproductive performance and biomarkers Pearson Correlation Coefficients
Prob > |r| under H0: Rho = 0
Number of Observations

| | TB | BA | PerStillborn | PerMummies | CalTotalWean | SubTB | SubBA | SubPerStillborn | SubMummies |
|---|---|---|---|---|---|---|---|---|---|
| Pre_IFNgammatrans | 0.15896 | 0.08215 | 0.08276 | 0.16434 | 0.07824 | 0.15975 | 0.06950 | −0.04250 | 0.13805 |
| | 0.361735 | 0.639035 | 0.636535 | 0.345535 | 0.655035 | 0.407829 | 0.720229 | 0.826729 | 0.475129 |
| Pre_TNFtrans | −0.10913 | −0.19964 | 0.15168 | 0.12651 | −0.29644 | −0.09729 | −0.05160 | 0.33159 | −0.39176 |
| | 0.532635 | 0.250235 | 0.384435 | 0.469035 | 0.083835 | 0.615629 | 0.790429 | 0.078929 | 0.035629 |
| Pre_TRAILtrans | 0.18092 | 0.10464 | 0.24253 | 0.08268 | 0.16063 | 0.49644 | 0.49575 | −0.24728 | −0.02925 |
| | 0.298335 | 0.549735 | 0.160435 | 0.636835 | 0.356635 | 0.006229 | 0.006229 | 0.195929 | 0.880329 |
| Wean_IFNgammatrans | 0.26156 | 0.22978 | 0.00430 | 0.08475 | 0.30193 | 0.22642 | 0.07254 | −0.01265 | 0.19577 |
| | 0.129135 | 0.184235 | 0.980535 | 0.628335 | 0.077935 | 0.237629 | 0.708429 | 0.948129 | 0.308829 |
| Wean_TNFtrans | −0.04202 | −0.08152 | 0.08754 | 0.04560 | −0.11449 | −0.12353 | −0.04353 | 0.37000 | −0.45078 |
| | 0.810635 | 0.641535 | 0.617035 | 0.794835 | 0.512535 | 0.523229 | 0.822629 | 0.048229 | 0.014129 |
| Wean_TRAILtrans | 0.13248 | 0.09820 | 0.16013 | −0.01024 | 0.03776 | 0.29289 | 0.30582 | −0.12183 | −0.11493 |
| | 0.448135 | 0.574735 | 0.358135 | 0.953535 | 0.829535 | 0.123129 | 0.106729 | 0.529029 | 0.552729 |

Example 2: Effect of Dietary Clay Fed to Sows Three Weeks Prior to Farrowing

Experimental Design, Procedures, and Data Collection

Animal Housing

Sows were individually housed in gestation stalls after mating and fed once per day based on their respective body condition score via a feed/water trough throughout the gestation period. Water was available on an ad libitum basis. On approximately d 112 of gestation, sows were moved to the farrowing barn and placed randomly in farrowing crates. Diets were changed from gestation to lactation diets and were fed ad libitum for the entire lactation period.

Dietary Treatments

Dietary treatments began approximately 93 days after mating. Every 10 sows located in the adjacent stalls were considered one subgroup. On the first day of the experiment, each subgroup was randomly assigned to one of 2 treatments with top-dressing of products provided for treatment 2 (Table 3). One off-test sow was placed between each subgroup to prevent the mixture of experimental diets. To identify the treatments, each on-test sow was marked using the spray marker on the corner of their sow ID cards according to their assigned color.

Experimental Diets

Basal diets (Table 4) were standard gestation and lactation diets without the addition of betaGRO®, yeast, or other clay-based technologies. Treatment 2 was delivered to sows by top-dressing using the designated teaspoons. During the late gestation period, top-dressing was performed daily by dropping products in front of the feed/water trough at prescribed rate when feeding in the morning. Aisles are swept of feed prior to water delivery.

After farrowing and throughout the entire lactation period, top-dressing of products at the rate prescribed for lactation was performed daily until weaning. On the day of weaning, sows were returned to the gestation barn and monitored for days from weaning to estrus.

TABLE 4

Dietary composition of basal diets

| Ingredient, AF | Gestation | Lactation |
|---|---|---|
| Corn - Fine Ground | 1,522.88 | 1,262.96 |
| Soybean meal | 297.45 | 599.22 |
| Dried distillers grains | N/A | N/A |
| Salt | 12.00 | 12.00 |
| Calcium Carbonate 38% | 26.48 | 15.61 |
| Phosphate - Mono Dicalcium | 25.82 | 23.02 |
| Fat - Fancy Tallow | 2.58 | 71.40 |
| L-Lysine HCL 78.8% | N/A | 3.24 |

TABLE 4-continued

Dietary composition of basal diets

| Ingredient, AF | Gestation | Lactation |
|---|---|---|
| DL Methionine-Dry 99% | N/A | N/A |
| Threonine | N/A | 0.71 |
| Tryptophan 100% | N/A | N/A |
| Phytase | 0.28 | 0.35 |
| Tribasic Copper Chloride | N/A | N/A |
| Sow VTM w/Choline | 5.00 | 5.00 |
| Wheat Midds | 100.00 | N/A |
| Choline Chloride - 60 | 1.02 | N/A |
| SALCURB | 6.50 | 6.50 |
| Total | 2,000.00 | 2,000.00 |
| Nutr. Composition | | |
| Crude Protein, % | 13.22 | 18.70 |
| Fat, % | 2.66 | 5.65 |
| SW NE, kcal/kg | 2,250.00 | 2,400.00 |
| Lysine, % | 0.65 | 1.15 |
| SW SI dig Lys, % | 0.57 | 1.04 |
| Mean Diam, microns | 380.72 | 315.74 |
| Calcium, % | 0.81 | 0.61 |
| Phosphorus, % | 0.60 | 0.58 |
| Ca/P Ratio, ratio | 1.35 | 1.05 |
| SW dig P, % | 0.41 | 0.43 |

[1] Diets updated 19 May 2016.

Data Collection

Reproductive and Litter Performance:

Individual sow body weight was measured (1) on the day sows were transferred to the farrowing barn, and (2) at weaning. The data was used to calculate the body weight loss during the lactation period using the formula: Sow BW Loss=Wean−(PRE−(LW+LW/5.5)), where Wean=sow weight at weaning; PRE=sow pre-farrow weight; LW=litter weight; LW/5.5=estimated placental weight. Days of lactation and days from weaning to estrus was recorded. Sow feed intake was measured during lactation for at least 20 sows/treatment (at least 40 sows measured) via Gestal Solo system. The number of piglets born (alive and dead), individual birth weight (alive and dead), individual weaning weight, and the number of dead piglets during lactation were recorded for each litter. Cross-fostering and removal of unthrifty pigs was allowed within 24 days after birth and only within treatments or to non-test litters.

Statistical Analysis

Data was analyzed using ANOVA by the MIXED procedure of SAS. Sow/litter served as the experimental unit. The statistical model included fixed effect of dietary treatments and a covariate of parity. Multiple comparisons between treatments were performed using the Tukey adjustment option of SAS. All results were reported as least squares means. The significance level chosen was α=0.05. Treatment effect was considered significant if P<0.05, whereas values between 0.05≤P≤0.10 were considered as statistical trends.

Results

Sows fed diets containing clay had greater (P<0.05) number of born alive, litter birth weight, calculated total wean, calculated litter weaning weight, and calculated litter weight gain without sow BW change compared to sows fed control diets (Table 5). Sows fed diets containing clay had lower (P<0.05) percent of mummies compared to sows fed the control diets. Sows fed diets containing clay tended (0.05<P<0.10) to have greater number of total-born pigs and calculated litter weight gain with sow BW change.

CONCLUSION

The objective of this trial was to determine the effects of feeding clay at 2.0 lb/ton through late gestation and lactation on sow and litter performance and sow fecal shedding of E. coli compared to sows fed basal diets. Feeding clay at 2.0 lb/ton had a positive and significant impact on the born alive, mummy percentage, litter birth weight calculated number weaned, and calculated litter gain weight. Adding clay to sow diets did not negatively impact any measurement, and there were no treatment differences in the fecal measurements.

TABLE 5

Effect of feeding clay to sows on reproductive performance

| Item | Control | Clay[1] | PSE | P-value |
|---|---|---|---|---|
| Reproductive performance of sows | | | | |
| # of Sows | 104 | 99 | N/A | N/A |
| Parity | 4.6 | 4.2 | 0.2 | 0.28 |
| Total born | 13.6 | 14.5 | 0.4 | 0.06 |
| Born alive | 12.4 | 13.6 | 0.4 | 0.02 |
| Stillborn, % | 5.4 | 4.9 | 0.8 | 0.59 |
| Mummies, % | 3.1 | 1.7 | 0.6 | 0.03 |
| Litter birth weight, lb | 36.2 | 39.3 | 1.1 | 0.02 |
| Pig birth weight,[2] lb | 2.80 | 2.87 | 0.05 | 0.23 |
| Pigs with birth weight < 2.5 lb, % | 27.1 | 26.2 | N/A | 0.61 |
| Pre-weaning mortality, % | 6.5 | 5.9 | 1.2 | 0.66 |
| Calculated total wean[3] | 11.6 | 12.6 | 0.4 | 0.02 |
| Lactation length, day | 17.7 | 17.8 | 0.2 | 0.55 |
| Pig weaning weight,[4] lb | 11.07 | 11.32 | 0.18 | 0.23 |
| CV of pig weaning weight, % | 20.3 | 19.3 | N/A | 0.96 |
| Calculated litter weaning weight,[4,5] lb | 131.2 | 144.0 | 4.9 | 0.02 |
| Calculated litter weight gain,[4] lb/day (without sow BW change) | 5.3 | 5.9 | 0.2 | 0.03 |
| Calculated litter weight gain (with sow BW change),[4] lb/day | 5.6 | 6.3 | 0.3 | 0.07 |
| Sow body weight change,[4] lb | 9.3 | 13.6 | 4.0 | 0.33 |
| % of sows lost weight | 50.0 | 45.5 | N/A | 0.64 |
| Wean-estrus intervals[4] | 5.0 | 4.5 | 0.3 | 0.29 |
| % sows with wean-estrus > 7 days | 4.8 | 3.0 | N/A | 0.52 |
| Culled sows, % | 22.1 | 14.1 | N/A | 0.18 |
| Sow lactation feed consumption[4] | | | | |
| # of Sows | 22 | 23 | N/A | N/A |
| % of Sows with feed measurement in lactation | 21.2 | 23.2 | N/A | N/A |
| Parity | 4.7 | 3.7 | 0.5 | 0.17 |
| Lactation length, day | 17.8 | 17.9 | 0.3 | 0.86 |
| ADFI, lb/day | 11.35 | 10.98 | 0.30 | 0.35 |
| Fecal measurements of sows | | | | |
| # of Sows | 30 | 30 | N/A | N/A |
| % of Sows with fecal measurements | 28.8 | 30.3 | N/A | N/A |
| Parity | 3.97 | 4.00 | 0.42 | 0.96 |
| Fecal measurements prior to farrow | | | | |
| Total E. coli., log cfu/g | 7.64 | 7.53 | 0.16 | 0.51 |
| ETEC, log cfu/g | 6.64 | 6.21 | 0.72 | 0.57 |
| F18,[6] log cfu/g | 0.00 | 0.00 | N/A | N/A |
| Total Clostridia, log cfu/g | 7.65 | 7.82 | 0.11 | 0.13 |
| C. perfringens Type A, log cfu/g | 5.27 | 6.48 | 0.93 | 0.22 |
| Fecal measurements at weaning | | | | |
| Total E. coli, log cfu/g | 6.67 | 6.25 | 0.29 | 0.22 |
| ETEC, log cfu/g | 3.94 | 3.09 | 0.75 | 0.32 |

TABLE 5-continued

Effect of feeding clay to sows on reproductive performance

| Item | Control | Clay[1] | PSE | P-value |
|---|---|---|---|---|
| F18,[7] log cfu/g | 0.04 | 0.38 | 0.47 | 0.52 |
| Total Clostridia, log cfu/g | 6.32 | 6.14 | 0.33 | 0.63 |
| *C. perfringens* Type A, log cfu/g | 4.33 | 5.07 | 0.77 | 0.40 |

[1]Clay was top-dressed at 2 lb/ton of complete feed in gestation and lactation. Top dressing started at day 93 of gestation and continued through entire lactation.
[2]Number of born alive was used as covariate in the statistical model
[3]Calculated total wean = born alive × (1-PWM/100)
[4]Lactation length was used as covariate in the statistical model
[5]Calculated litter weaning weight = pig weaning wt × calculated total wean
[6]None of the samples had a detectable level of F18 count
[7]One sample from Control treatment and three samples from Clay treatment had a detectable level of F18 count

Example 3: Effect of Adding Clay to Sow Diets During Gestation and Lactation on Reproductive and Litter Performance Experimental Design, Procedures, and Data Collection
Animal Housing Sows were individually housed in gestation stalls after mating and fed once per day based on their respective body condition score via a feed/water trough throughout the gestation period. Water was available on an ad libitum basis. On approximately d 112 of gestation, sows were moved to the farrowing barn and placed randomly in farrowing crates. Diets were changed from gestation to lactation diets and were fed ad libitum for the entire lactation period.

Dietary Treatments

Dietary treatments began approximately 94 days after mating. Every 10 sows located in the adjacent stalls were considered one subgroup. On the first day of the experiment, each subgroup was randomly assigned to one of 4 treatments with top-dressing of products provided for treatments 2 through 4 (Table 6). One off-test sow was placed between each subgroup to prevent the mixture of experimental diets.

TABLE 6

Dietary treatments and assigned colors for sows.

| Treatment | Additive | Inclusion Rate | No. of sows |
|---|---|---|---|
| 1. Control | None | None | 120 |
| 2. Clay_0.5 | Clay[3] | 0.5 lb/ton | 120 |
| 3. Clay_1.0 | Clay[3] | 1.0 lb/ton | 120 |
| 4. Clay_1.5 | Clay[3] | 1.5 lb/ton | 120 |
|  |  |  | 480 |

[1]Calculated based on the assumption that the average feed intake is 5.0 lb/day in gestation.
[2]Calculated based on the assumption that the average feed intake is 10.0 lb/day in lactation.
[3]2 lb version (rather than 4 lb version) of therapeutic clay used for the study.

Experimental Diets

Basal diets (Table 7) were standard gestation and lactation diets. Treatments 2 through 4 were delivered to sows by top-dressing using the designated teaspoons. During the late gestation period, top-dressing was performed daily by dropping products in front of the feed/water trough at prescribed rate when feeding in the morning. Aisles are swept of feed prior to water delivery.

After farrowing and throughout the entire lactation period, top-dressing of products at the rate prescribed for lactation was performed daily until weaning. On the day of weaning, sows were returned to the gestation barn and monitored for days from weaning to estrus.

TABLE 7

Dietary composition of basal diets

| Ingredient, lb | Gestation Diet[1] | Lactation Diet[1] |
|---|---|---|
| Corn | 1397.44 | 1016.28 |
| Distillers dried grains | 265.83 | 352.54 |
| Soybean meal | 104.26 | 479.56 |
| Salt | 10.55 | 10.05 |
| Phosphate - Mono Dicalcium | 21.89 | 17.12 |
| Calcium carbonate | 22.57 | 19.57 |
| L-lysine HCL 78.8% | 5.04 | 5.92 |
| Choline Chloride - 60 | 3.17 | 1.22 |
| Sow VTM w/Choline | 5.00 | 5.00 |
| Phytase | 0.30 | 0.30 |
| Wheat Midds | 157.45 | — |
| Fat - corn oil | — | 85.94 |
| SAL CURB | 6.50 | 6.50 |
| Total | 2000.00 | 2000.00 |
| Calculated nutrient composition | | |
| Crude Protein, % | 12.87 | 20.51 |
| Fat, % | 3.24 | 7.21 |
| SW NE, kcal/kg | 2210.00 | 2400.00 |
| Lysine, % | 0.69 | 1.22 |
| SW SI dig Lys, % | 0.57 | 1.05 |
| Mean Diam, microns | 385.69 | 280.49 |
| Ca, % | 0.81 | 0.75 |
| P, % | 0.60 | 0.56 |
| Ca/P Ration | 1.35 | 1.35 |
| SW dig P, % | 0.46 | 0.44 |

[1]Diets included 400 ppm CTC and 35 ppm Denagard.

Data Collection
Reproductive and Litter Performance:

Individual sow body weight was measured (1) on the day sows were transferred to the farrowing barn, and (2) at weaning. The data was used to calculate the body weight loss during the lactation period using the formula: Sow BW Loss=Wean−(PRE−(LW+LW/5.5)), where Wean=sow weight at weaning; PRE=sow pre-farrow weight; LW=litter weight; LW/5.5=estimated placental weight (Fahmy, 1971). Days of lactation and days from weaning to estrus was recorded. Sow feed intake was measured during lactation for at least 20 sows/treatment (at least 80 sows measured) via Gestal Solo system. The number of piglets born (alive and dead), individual birth weight (alive and dead), individual weaning weight, and the number of dead piglets during lactation were recorded for each litter. Cross-fostering and removal of unthrifty pigs was allowed within 24 days after birth and only within treatments or to non-test litters. Creep feeding was not offered during this trial, but access to the sow feed was not restricted.

Statistical Analysis

Data was analyzed using ANOVA by the MIXED procedure of SAS. Sow/litter served as the experimental unit. The statistical model included fixed effect of dietary treatments and a covariate of parity. Multiple comparisons between treatments were performed using the Tukey adjustment option of SAS. All results were reported as least squares means. The significance level chosen was $\alpha=0.05$. Treatment effect was considered significant if P<0.05, whereas values between $0.05 \leq P \leq 0.10$ were considered as statistical trends.

Results

Sows fed increasing levels of clay had a linear improvement in birth weight (P<0.10; Table 8). Preweaning mortality was reduced P<0.06) in sows fed 1 lb/ton, and feed intake (P=0.06) compared to sows fed 0.5 lb/ton. Feed intake was increased (P=0.06) during lactation for sows fed 1.5 lb of clay/ton, and overall intake increased linearly (P<0.005) as the inclusion of clay increased in the diet.

Sows fed diets containing clay at 0.5 lb/ton had a lower (P=0.02) cull rate compared to Control sows. Sows fed diets containing clay at 0.5 lb/ton tended (0.05<P<0.10) have a lower cull rate compared to sows fed diets containing clay at 1.0 lb/ton and was lower (P=0.02) than sows fed diets containing clay at 1.5 lb/ton.

Example 4: Feeding Clay to Sows Improves Litter Size at Birth and at Weaning The effect of feeding Clay to sows during gestation and lactation was evaluated to determine the effect on reproductive performance. Sows (parity ≥2) were randomly selected from a commercial herd were allotted to either a Control diet (CON) or a diet containing Clay at 4.0 lb/ton, resulting in 97 sows for CON and 95 sows for Clay treatment. Dietary treatments started on day 3 after breeding and continued to the end of lactation through top-dressing clay to the basal diet (Table 8 and 9). Individual sow body weight was measured on the day when sows were transferred to the farrowing crate and at weaning to calculate body weight change during lactation period using the formula Sow BW Change=Wean−(PRE−(LW+LW/5.5)), where Wean=sow weight at weaning; PRE=sow pre-farrow weight; LW=litter weight; LW/5.5=estimated placental weight. Lactation length and wean to estrus interval were recorded. The number of piglets born (alive and dead), individual pig birth weight (alive and dead), individual pig weaning weight, and the number of piglets dead during lactation were recorded for each litter. Cross-fostering and pull of starves were allowed within 2 days after birth and only within treatments or to the non-test litters. In addition, piglet management, including tail docking, iron injection, male piglet castration, were performed. Piglets' access to the sow feed was not restricted.

TABLE 8

Effect of clay titration on sow and litter performance

| | Treatment, lb/ton | | | | | P-values | | |
|---|---|---|---|---|---|---|---|---|
| Item | Control | 0.5 | 1.0 | 1.5 | PSE | P-overall | P-linear | P-quadratic |
| # Total Litters | 107 | 114 | 107 | 112 | N/A | N/A | N/A | N/A |
| Total born per litter | 14.6 | 14.8 | 14.1 | 14.4 | 0.5 | 0.49 | 0.35 | 0.83 |
| Born alive per litter | 13.5 | 14.0 | 13.3 | 13.6 | 0.5 | 0.44 | 0.57 | 0.53 |
| % Stillborns | 4.1 | 2.7 | 2.9 | 3.1 | 1.0 | 0.43 | 0.42 | 0.29 |
| % Mummies | 2.7 | 2.4 | 2.2 | 2.1 | 0.7 | 0.83 | 0.39 | 0.39 |
| Litter birth wt, lb | 38.3 | 39.7 | 38.4 | 39.2 | 1.2 | 0.53 | 0.80 | 0.80 |
| Pig birth wt (adj for born alive), lb | 2.88 | 2.91 | 2.92 | 2.96 | 0.06 | 0.59 | 0.16 | 0.69 |
| Measurement of feed intake during lactation | | | | | | | | |
| # Sows measured | 23 | 25 | 32 | 25 | N/A | N/A | N/A | N/A |
| Lactation days of sows measured, day | 19.0 | 18.5 | 18.1 | 18.3 | 0.3 | 0.12 | N/A | N/A |
| ADFI of sows measured, lb/day | 11.92 | 12.88 | 12.69 | 13.18 | 0.43 | 0.09 | 0.03 | 0.53 |
| At Weaning | | | | | | | | |
| Calculated total wean per litter | 12.9 | 13.1 | 12.9 | 12.9 | 0.4 | 0.93 | 0.68 | 0.41 |
| % PWM | 4.2 | 5.9 | 3.2 | 5.0 | 1.2 | 0.08 | 0.99 | 0.65 |
| Lactation days, day | 18.0 | 18.6 | 18.4 | 18.2 | 0.2 | 0.07 | N/A | N/A |
| Litter weaning wt (adj for lactation days), lb | 134.1 | 132.2 | 135.7 | 130.4 | 3.5 | 0.36 | 0.56 | 0.15 |
| Litter weight gain/day, lb | 5.2 | 5.1 | 5.3 | 4.9 | 0.2 | 0.23 | 0.46 | 0.19 |
| Pig weaning wt (adj for lactation days), lb | 12.5 | 12.4 | 12.5 | 12.3 | 0.2 | 0.68 | 0.47 | 0.38 |
| Wean-estrus intervals, d | 4.6 | 5.1 | 4.4 | 4.5 | 0.5 | 0.30 | 0.40 | 0.61 |
| % Culled Sows | 11.2 | 2.6 | 8.4 | 10.7 | N/A | 0.09 | N/A | N/A |
| Sow BW change during lactation, lb | 3.2 | 2.2 | 5.7 | 9.3 | 5.5 | 0.48 | 0.19 | 0.37 |
| Percentage of sow BW change during lactation, % | 0.8 | 0.6 | 1.1 | 1.8 | 0.9 | 0.52 | 0.22 | 0.34 |

Example 4: Effect of Feeding Clay to Sows in Gestation and Lactation on Litter Performance Experimental Design, Procedures, and Data Collection
Animal Housing Sows were individually housed in gestation stalls after mating and fed once per day based on their respective body condition score via a feed/water trough throughout the gestation period. Water was available on an ad libitum basis. On approximately d 112 of gestation, sows were moved to the farrowing barn and placed randomly in farrowing crates. Diets were changed from gestation to lactation diets and were fed ad libitum for the entire lactation period.

Dietary Treatments

Dietary treatments began approximately 3 days after mating. Every 10 sows located in the adjacent stalls were considered one subgroup. On the first day of the experiment, each subgroup was randomly assigned to one of 4 treatments with top-dressing of products provided for treatments 2 through 4 (Table 9). One off-test sow was placed between each subgroup to prevent the mixture of experimental diets.

TABLE 9

Dietary treatments and assigned colors for sows.

| Treatment | Additive | Inclusion Rate | No. of sows |
|---|---|---|---|
| 1. Control | None | — | 101 |
| 2. Clay | therapeutic clay | 2.0 lb/ton[3] | 105 |
| 3. phytogenic | Phytogenic | 0.4 lb/ton[4] | 105 |
| 4. Clay + phytogenic | therapeutic clay + phytogenic | 2.0 lb/ton + 0.4 lb/ton, resp. | 95 |
| | | Total | 406 |

[1]Calculated based on the assumption that the average feed intake is 5.0 lb/day in gestation.
[2]Calculated based on the assumption that the average feed intake is 10.0 lb/day in lactation.
[3]NQ therapeutic clay ore was given at a daily inclusion of rate 2.27 g/day + 1:1 inclusion of ground corn (total 4.54 g/day) during gestation.
[4]Phytogenic was given at a daily inclusion rate of 0.45 g/day + 1:1 inclusion of ground corn (total 0.90 g/day) during gestation.

Experimental Diets

Basal diets were standard gestation and lactation diets used by NHF (Table 10A and Table 10B). Treatments 2 through 4 were delivered to sows by top-dressing using the designated teaspoons/tablespoons. During the gestation period, top-dressing was performed daily by dropping products in front of the feed/water trough at prescribed rate when feeding in the morning. Aisles are swept of feed prior to water delivery.

After farrowing and throughout the entire lactation period, top-dressing of products at the rate prescribed for lactation was performed daily until weaning. On the day of weaning, sows were returned to the gestation barn and monitored for days from weaning to estrus.

TABLE 10A

Dietary composition of basal diets until

| Ingredient | Gestation[1] | Lactation[2] |
|---|---|---|
| Corn - Fine Ground | 1,014.51 | 1,214.08 |
| Soybean meal | 60.00 | 619.87 |
| Distillers dried grains | 800.00 | N/A |
| Salt | 12.00 | 12.00 |
| Calcium Carbonate 38% | 34.21 | 24.81 |
| Fat - Fancy Tallow | N/A | 85.85 |
| L-Lysine HCL 78.8% | 7.56 | 5.88 |
| DL Methionine-Dry 99% | N/A | N/A |
| Threonine | 0.23 | 0.68 |
| Tryptophan 100% | 0.36 | N/A |
| Phytase | 0.35 | 0.35 |
| Tribasic Copper Chloride | N/A | N/A |
| Sow VTM w/Choline | 5.00 | 5.99 |
| TIAMULIN 10 g/lb | N/A | 3.50 |
| CTC-AUREOMY-90 g/lb | N/A | 4.40 |
| SALCURB | 6.50 | 6.50 |
| Thiamine 10 Gr/Lb | 0.45 | N/A |
| Feed Aid | 3.00 | N/A |
| Sow Platform | N/A | N/A |
| Phosphate - Mono Dicalcium | 11.87 | 23.99 |
| Wheat Midds | 43.98 | N/A |
| Amount Per Ton | 2,000.00 | 2,000.00 |
| Cost/Ton ($, As Fed) | 140.71 | 211.44 |
| Nutrient, As Fed Conc | | |
| Crude Protein, % | 16.48 | 18.81 |
| Fat, % | 3.91 | 6.23 |
| Mean Diam, microns | 253.63 | 303.52 |
| Calcium, % | 0.81 | 0.80 |
| Phosphorus, % | 0.60 | 0.60 |
| Ca/P Ratio, ratio | 1.35 | 1.35 |
| SW dig P, % | 0.49 | 0.44 |
| SW NE, kcal/kg | 2,156.32 | 2,400.00 |
| Lysine, % | 0.82 | 1.26 |
| SW SI dig Lys, % | 0.69 | 1.15 |
| Added Salt, % | 0.60 | 0.60 |
| Calcium for Tag, % | 0.80 | 0.80 |

[1]Gestation diets updated October 2017
[2]Lactation diets updated November 2017. CTC and Denagard provided during lactation at 400 g and 35 g, respectively.

TABLE 10B

Dietary composition of basal diets beginning Apr. 2, 2018.

| Ingredient | Gestation[1] | Lactation[2] |
|---|---|---|
| Corn - Fine Ground | 1,012.51 | 1,214.08 |
| Soybean meal | 60.00 | 619.87 |
| Distillers dried grains | 800.00 | N/A |
| Salt | 12.00 | 12.00 |
| Calcium Carbonate 38% | 34.21 | 24.81 |
| Fat - Fancy Tallow | N/A | 85.85 |
| L-Lysine HCL 78.8% | 7.56 | 5.88 |
| DL Methionine-Dry 99% | N/A | N/A |
| Threonine | 0.23 | 0.68 |
| Tryptophan 100% | 0.36 | N/A |
| Phytase | 0.35 | 0.35 |
| Tribasic Copper Chloride | N/A | N/A |
| Sow VTM w/Choline | 5.00 | 5.99 |
| TIAMULIN 10 g/lb | N/A | 3.50 |
| CTC-AUREOMY-90 g/lb | N/A | 4.40 |
| SALCURB | 6.50 | 6.50 |
| Thiamine 10 Gr/Lb | 0.45 | N/A |
| Feed Aid | N/A | N/A |
| Defusion Plus | 5.00 | N/A |
| Phosphate - Mono Dicalcium | 11.87 | 23.99 |
| Wheat Midds By-Product 27-34% NDF | 43.98 | N/A |
| Amount Per Ton | 2,000.00 | 2,000.00 |
| Cost/Ton ($, As Fed) | 140.71 | 211.44 |
| Nutrient, As Fed Conc | | |
| Crude Protein, % | 16.48 | 18.81 |
| Fat, % | 3.91 | 6.23 |
| Mean Diam, microns | 253.63 | 303.52 |
| Calcium, % | 0.81 | 0.80 |
| Phosphorus, % | 0.60 | 0.60 |
| Ca/P Ratio, ratio | 1.35 | 1.35 |
| SW dig P, % | 0.49 | 0.44 |
| SW NE, kcal/kg | 2,156.32 | 2,400.00 |
| Lysine, % | 0.82 | 1.26 |

TABLE 10B-continued

Dietary composition of basal diets beginning Apr. 2, 2018.

| Ingredient | Gestation[1] | Lactation[2] |
|---|---|---|
| SW SI dig Lys, % | 0.69 | 1.15 |
| Added Salt, % | 0.60 | 0.60 |
| Calcium for Tag, % | 0.80 | 0.80 |

[1]Gestation diets updated April 2018.
[2]Lactation diets updated November 2017. CTC and Denagard provided during lactation at 400 g and 35 g, respectively.

Data Collection
Reproductive and Litter Performance:

Individual sow body weight was measured (1) on the day sows were transferred to the farrowing barn, and (2) at weaning. The data was used to calculate the body weight loss during the lactation period using the formula: Sow BW Loss=Wean−(PRE−(LW+LW/5.5)), where Wean=sow weight at weaning; PRE=sow pre-farrow weight, LW=litter weight; LW/5.5=estimated placental weight (Fahmy. 1971). Days of lactation and days from weaning to estrus was recorded. The number of piglets born (alive and dead), individual birth weight (alive and dead), individual weaning weight, and the number of dead piglets during lactation were recorded for each litter. Cross-fostering and removal of unthrifty pigs was allowed within 24 days after birth and only within treatments or to non-test litters. Lactation feed intake was monitored for a subset of sows with Jyga Gestal Solo® electronic sow feeders.

Samples:

Collected blood samples from sows prior to farrow and at weaning from 25 sows/treatment. Day of gestation and lactation were recorded for each sampling sow. Sow parities were balanced into 3 subgroups: P2-4, 5-7, and 8+. Collected blood samples from 2 piglets (gilt and barrow) at day 2 of age and at weaning and 25 litters/treatment. Age and individual weights at collection were recorded. Colostrum samples were collected from Treatments 1 and 4 (25 sows/treatment) within 24 hours of farrowing. Colostrum samples were not analyzed at this time.

Statistical Analysis

Data was analyzed using ANOVA by the MIXED procedure of SAS. Sow/litter served as the experimental unit. The statistical model included fixed effect of dietary treatments and a covariate of parity. Multiple comparisons between treatments were performed using the Tukey adjustment option of SAS. All results were reported as least squares means. The significance level chosen was $\alpha=0.05$. Treatment effect was considered significant if $P<0.05$, whereas values between $0.05 \leq P \leq 0.10$ were considered as statistical trends.

Results

Sows fed clay had increased ($P<0.05$) number of total-born pigs, live born pigs and heavier birth weights than the control fed sows (Table 11). The number of pigs born less than 1.7 lbs was reduced ($P<0.05$) for sows fed clay compared to sows fed a control diet. The number of abortions was reduced ($P<0.05$) for sows fed clay compared to sows fed the control diet. The improvements in total pigs born alive for sows fed clay-based diets resulted in increased number of pigs weaned as well.

TABLE 11

Summary 2017-006 therapeutic clay × phytogenic long term sow study

| | Main effect of therapeutic clay | | Main effect of phytogenic | | No therapeutic clay | | therapeutic clay | |
|---|---|---|---|---|---|---|---|---|
| | No | | | | No | | No | |
| Item | No therapeutic clay | therapeutic clay | No phytogenic | phytogenic | No phytogenic | phytogenic | No phytogenic | phytogenic |
| # of Sows | 206 | 200 | 206 | 200 | 101 | 105 | 105 | 95 |
| Parity[1] | 5.0 | 5.0 | 5.1 | 4.9 | 5.1 | 4.8 | 5.0 | 5.0 |
| Conception rate, % | 98.1 | 97.7 | 97.3 | 98.5 | 97.7 | 98.5 | 96.9 | 98.5 |
| Farrowing rate, % | 90.8 | 88.1 | 88.5 | 90.4 | 87.7$^c$ | 93.8$^d$ | 89.2$^{cd}$ | 86.9$^c$ |
| Culled sows due to vaginal discharge, % | 2.3 | 5.4 | 4.6 | 3.1 | 3.8$^{ab}$ | 0.8$^a$ | 5.4$^b$ | 5.4$^b$ |
| Sows aborted, % | 3.1 | 1.5 | 1.2 | 3.5 | 2.3$^b$ | 3.8$^b$ | 0.0$^a$ | 3.1$^b$ |
| Reproductive performance | | | | | | | | |
| Total born | 14.1 | 14.7 | 14.4 | 14.4 | 13.7$^a$ | 14.4$^{ab}$ | 15.0$^b$ | 14.4$^{ab}$ |
| Born alive[2] | 13.1 | 13.7 | 13.4 | 13.4 | 12.8$^a$ | 13.3$^{ab}$ | 13.9$^b$ | 13.5$^{ab}$ |
| Stillborns, % | 4.0 | 4.3 | 4.1 | 4.2 | 3.5 | 4.5 | 4.7 | 3.8 |

TABLE 11-continued

Summary 2017-006 therapeutic clay × phytogenic long term sow study

| | | | | | | | | |
|---|---|---|---|---|---|---|---|---|
| Mummies, % | 2.9 | 2.3 | 2.4 | 2.8 | 2.6 | 3.3 | 2.2 | 2.4 |
| Total of stillborns and mummies, % | 7.0 | 6.5 | 6.5 | 7.0 | 6.1 | 7.8 | 6.9 | 6.1 |
| Litter birth weight, lb | 39.5 | 41.4 | 40.4 | 40.5 | $38.8^a$ | $40.34^{ab}$ | $42.1^b$ | $40.8^{ab}$ |
| Pig birth weight, lb | 2.99 | 3.06 | 3.02 | 3.04 | 2.97 | 3.01 | 3.06 | 3.06 |
| Percentage of pigs with birth weight < 1.7 lb, % | 6.1 | 5.5 | 5.7 | 5.9 | $6.6^a$ | $5.6^{ab}$ | $4.9^a$ | $6.3^{ab}$ |
| Pre-weaning mortality, % | 8.7 | 8.9 | 8.6 | 8.9 | 8.6 | 8.8 | 8.7 | 9.1 |
| Piglets dead due to low viability % | 3.2 | 2.8 | 3.2 | 2.8 | 3.4 | 3.0 | 3.0 | 2.6 |
| Calculated total wean | 11.9 | 12.4 | 12.2 | 12.2 | $11.6^a$ | $12.1^{ac}$ | $12.7^a$ | $12.2^{ab}$ |
| Lactation length$^a$ day | 19.3 | 19.1 | 19.2 | 19.3 | 19.2 | 19.5 | 19.1 | 19.1 |
| Pig weaning weight lb | 12.4 | 12.1 | 12.2 | 12.3 | 12.3 | 12.4 | 12.1 | 12 1 |
| Litter weaning weight, lb | 146.1 | 149.2 | 147.6 | 147.6 | 143.7 | 148.5 | 151.6 | 146.8 |
| Wean-estrus intervals, day | 4.8 | 4.9 | 4.7 | 5.0 | 4.7 | 4.9 | 4.8 | 5.1 |
| Sow BW change during lactation, lb | 12.6 | 7.7 | 9.4 | 10.9 | $15.3^a$ | $10.0^{ab}$ | $3.6^a$ | $11.7^{ab}$ |
| Sow BW change during lactation, % | 2.5 | 1.5 | 1.9 | 2.1 | $3.0^a$ | $1.9^{ab}$ | $0.9^b$ | $2.2^{ab}$ |

TABLE 11-continued

Summary 2017-006 therapeutic clay × phytogenic long term sow study

| Sow body weight prior to farrow, lb | 562 | 569 | 567 | 564 | 560 | 563 | 573 | 564 |
| --- | --- | --- | --- | --- | --- | --- | --- | --- |
| Sow body weight at weaning, lb | 525 | 525 | 525 | 524 | 527 | 523 | 524 | 525 |
| % of sows lost weight | 34.5 | 39.5 | 38.3 | 35.5 | 29.7$^a$ | 39.0$^{ac}$ | 46.7$^a$ | 31.6$^{ab}$ |

Sow feed intake during lactation

| # of Sows measured | 48 | 65 | 57 | 56 | 24 | 24 | 33 | 32 |
| --- | --- | --- | --- | --- | --- | --- | --- | --- |
| ADFi during lactation, lb/day | 14.7 | 14.3 | 14.4 | 14.5 | 14.8 | 14.6 | 14.1 | 14.5 |
| Sow BW change during lactation, lb | 11 | 0.3 | −0.5 | 1.9 | 1.9 | 0.2 | −3.0 | 3.7 |
| Sow BW change during lactation, % | 0.3 | 0.1 | 0.0 | 0.4 | 0.5 | 0.1 | −0.4 | 0.6 |
| Sow body weight prior to farrow, lb | 561 | 568 | 567 | 562 | 555 | 566 | 579 | 557 |
| Sow body weight at weaning, lb | 513 | 515 | 514 | 514 | 509 | 517 | 519 | 512 |

Piglet Immunocrit ratio

| At birth | 0.038 | 0.038 | 0.036 | 0.040 | 0.039$^{ab}$ | 0.037$^{ab}$ | 0.032$^a$ | 0.043$^c$ |
| --- | --- | --- | --- | --- | --- | --- | --- | --- |
| At weaning | 0.048 | 0.050 | 0.052 | 0.046 | 0.050 | 0.046 | 0.054 | 0.046 |
| ADG, lb/day | 0.52 | 0.51 | 0.52 | 0.51 | 0.54 | 0.50 | 0.50 | 0.52 |

Piglet serum cytokines
At birth

| IFN-α, pg/mL | N/A | N/A | N/A | N/A | 0.7 | N/A | 1.0 | N/A |
| --- | --- | --- | --- | --- | --- | --- | --- | --- |
| IL-1β, pg/mL | N/A | N/A | N/A | N/A | 19.7 | N/A | 66.0 | N/A |
| IL-6, pg/ml | N/A | N/A | N/A | N/A | 77.7 | N/A | 218.2 | N/A |
| IL-8, pg/mL | N/A | N/A | N/A | N/A | 37.2 | N/A | 67.5 | N/A |
| IL-12, pg/ml | N/A | N/A | N/A | N/A | 142 2 | N/A | 162.9 | N/A |

TABLE 11-continued

Summary 2017-006 therapeutic clay × phytogenic long term sow study

| | | | | | | | | |
|---|---|---|---|---|---|---|---|---|
| TNF-α, pg/mL | N/A | N/A | N/A | NA | 7.9 | N/A | 24.7 | N/A |

At weaning

| | | | | | | | | |
|---|---|---|---|---|---|---|---|---|
| IFN-α, pg/mL | N/A | N/A | N/A | N/A | 1.3 | N/A | 1.8 | N/A |
| IL-1β, pg/mL | N/A | N/A | N/A | N/A | 1.8 | N/A | 6.6 | N/A |
| IL-6, pg/ml | N/A | N/A | N/A | N/A | 13.2 | N/A | 33.3 | N/A |
| IL-8, pg/mL | N/A | N/A | N/A | N/A | 67.4 | N/A | 75.1 | N/A |
| IL-12, pg/ml | N/A | N/A | N/A | N/A | 488.7 | N/A | 593.6 | N/A |
| TNF-α, pg/mL | N/A | N/A | N/A | N/A | 2.0 | N/A | 2.3 | N/A |

| | P-value | | | |
|---|---|---|---|---|
| Item | PSE | therapeutic clay | phytogenic | therapeutic clay × phytogenic |
| # of Sows | N/A | N/A | N/A | N/A |
| Parity[1] | 0.2 | 0.90 | 0.43 | 0.45 |
| Conception rate, % | N/A | N/A | N/A | N/A |
| Farrowing rate, % | N/A | N/A | N/A | N/A |
| Culled sows due to vaginal discharge, % | N/A | N/A | N/A | N/A |
| Sows aborted, % | N/A | N/A | N/A | N/A |

Reproductive performance

| Item | PSE | therapeutic clay | phytogenic | therapeutic clay × phytogenic |
|---|---|---|---|---|
| Total born | 0.4 | 0.05 | 0.84 | 0.04 |
| Born alive[2] | 0.3 | 0.02 | 0.91 | 0.11 |
| Stillborns, % | 0.7 | 0.72 | 0.96 | 0.11 |
| Mummies, % | 0.5 | 0.15 | 0.36 | 0.62 |
| Total of stillborns and mummies, % | 0.9 | 0.57 | 0.57 | 0.13 |
| Litter birth weight, lb | 1.0 | 0.02 | 0.89 | 0.10 |
| Pig birth weight, lb | 0.05 | 0.12 | 0.65 | 0.62 |
| Percentage of pigs with birth weight < 1.7 lb, % | N/A | N/A | N/A | N/A |

TABLE 11-continued

| Summary 2017-006 therapeutic clay × phytogenic long term sow study ||||||
| --- | --- | --- | --- | --- | --- |
| Pre-weaning mortality, % | 1.0 | 0.86 | 0.72 | 0.92 |
| Piglets dead due to low viability % | 0.7 | 0.48 | 0.48 | 0.99 |
| Calculated total wean | 0.3 | 0.02 | 1.00 | 0.10 |
| Lactation length$^a$ day | 0.3 | 0.36 | 0.62 | 0.67 |
| Pig weaning weight, lb | 0.2 | 0.13 | 0.74 | 0.96 |
| Litter weaning weight, lb | 4.5 | 0.40 | 1.00 | 0.19 |
| Wean-estrus intervals, day | 0.4 | 0.67 | 0.38 | 0.96 |
| Sow BW change during lactation, lb | 3.5 | 0.09 | 0.62 | 0.02 |
| Sow BW change during lactation, % | 0.6 | 0.09 | 0.76 | 0.03 |
| Sow body weight prior to farrow, lb | 6 | 0.14 | 0.56 | 0.19 |
| Sow body weight at weaning, lb | 5 | 0.97 | 0.73 | 0.60 |
| % of sows lost weight | N/A | N/A | N/A | N/A |
| Sow feed intake during lactation ||||||
| # of Sows measured | N/A | N/A | N/A | N/A |

TABLE 11-continued

| Summary 2017-006 therapeutic clay × phytogenic long term sow study | | | | |
|---|---|---|---|---|
| ADFi during lactation, lb/day | 0.33 | 0.11 | 0.67 | 0.25 |
| Sow BW change during lactation, lb | 5.1 | 0.59 | 0.34 | 0.60 |
| Sow BW change during lactation, % | 0.9 | 0.69 | 0.35 | 0.60 |
| Sow body weight prior to farrow, lb | 10 | 0.39 | 0.54 | 0.06 |
| Sow body weight at weaning, lb | 9 | 0.80 | 0.93 | 0.32 |
| Piglet Immunocrit ratio | | | | |
| At birth | 0.004 | 0.84 | 0.05 | 0.01 |
| At weaning | 0.002 | 0.24 | 0.02 | 0.36 |
| ADG, lb/day | 0.02 | 0.49 | 0.70 | 0.09 |
| Piglet serum cytokines At birth | | | | |
| IFN-α, pg/mL | 2.2 | 0.15 | N/A | N/A |
| IL-1β, pg/mL | 118.7 | 0.06 | N/A | N/A |
| IL-6, pg/ml | 719.8 | 0.13 | N/A | N/A |
| IL-8, pg/mL | 12.3 | 0.01 | N/A | N/A |
| IL-12, pg/ml | 84.9 | 0.70 | N/A | N/A |
| TNF-α, pg/mL | 338.2 | 0.03 | N/A | N/A |
| At weaning | | | | |
| IFN-α, pg/mL | 1.0 | 0.17 | N/A | N/A |
| IL-1β, pg/mL | 41.7 | 0.001 | N/A | N/A |
| IL-6, pg/ml | 608.5 | 0.07 | N/A | N/A |
| IL-8, pg/mL | 10.0 | 0.57 | N/A | N/A |
| IL-12, pg/ml | 72.9 | 0.27 | N/A | N/A |
| TNF-α, pg/mL | 60.0 | 0.03 | N/A | N/A |

Example 5: Effect of Clay-Based Diets on Sow Performance by Parity

Sow performance data was reanalyzed to determine the response to feeding clay to sows based on parity (Table 12). Sows were sorted into 6 different parity groups; parity 2, 3, 4 & 5, 6 & 7, and 8 or greater. These data suggest that parity had a major impact on the level of response. Parity 2 sows and sows greater than 6 had a more pronounced improvement in total born and born alive compared to sows from parity 3, 4, and 5. These are usually parities that tend to result in lower performance due to health issues in parity 2 sows and age/health effects in parity 6 sows or older. The data suggest that adding clay to the diets is actually restoring performance to greater levels and improving the overall output of the sow herd.

TABLE 12

Effect of parity on the response to feeding clay-based diets for the entire gestation + lactation period in sows

| | All Sows | | | | Parity = 2 | | | | Parity = 3 | | | |
|---|---|---|---|---|---|---|---|---|---|---|---|---|
| Item | Control | therapeutic clay | PSE | P-value | Control | therapeutic clay | PSE | P-value | Control | therapeutic clay | PSE | P-value |
| # of Trials | 1 | 1 | | | 1 | 1 | | | 1 | 1 | | |
| # of Sows | 101 | 105 | | | 8 | 9 | | | 13 | 23 | | |
| Parity | 5.1 | 5.0 | 0.2 | 0.64 | | | | | | | | |
| Total born | 13.7 | 15.0 | 0.4 | 0.005 | 14.4 | 17.3 | 1.1 | 0.05 | 16.6 | 15.7 | 0.8 | 0.32 |
| Born alive | 12.8 | 13.9 | 0.3 | 0.005 | 13.0 | 15.7 | 1.0 | 0.02 | 15.8 | 14.7 | 0.8 | 0.19 |
| Stillborns, % | 3.5 | 4.7 | 0.7 | 0.17 | 6.2 | 8.0 | 2.1 | 0.66 | 3.4 | 3.5 | 1.6 | 0.99 |
| Mummies, % | 2.6 | 2.2 | 0.5 | 0.55 | 1.6 | 1.2 | 1.5 | 0.75 | 1.3 | 2.9 | 1.2 | 0.24 |
| Total of stillborns and mummies, % | 6.1 | 6.9 | 0.9 | 0.46 | 7.8 | 9.2 | 2.7 | 0.75 | 4.7 | 6.3 | 2.1 | 0.47 |
| Litter birth weight, lb | 38.8 | 42.1 | 1.0 | 0.003 | 40.6 | 49.9 | 2.8 | 0.005 | 49.9 | 46.7 | 2.2 | 0.16 |
| Pig birth weight, lb | 2.97 | 3.06 | 0.05 | 0.12 | 3.09 | 3.32 | 0.15 | 0.12 | 3.34 | 3.26 | 0.12 | 0.47 |
| Pre-weaning mortality, % | 8.6 | 8.7 | 1.0 | 0.83 | 11.5 | 8.8 | 2.9 | 0.68 | 7.4 | 6.7 | 2.3 | 0.77 |
| Total number of piglet weaned | 11.6 | 12.7 | 0.3 | 0.007 | 11.3 | 14.2 | 0.9 | 0.009 | 14.6 | 13.7 | 0.7 | 0.25 |
| Pig weaning weight, lb | 12.3 | 12.1 | 0.2 | 0.44 | 11.3 | 12.0 | 0.6 | 0.52 | 12.7 | 12.2 | 0.5 | 0.47 |
| Litter weaning weight, lb | 143.7 | 151.6 | 4.5 | 0.13 | 126.7 | 171.8 | 12.3 | 0.05 | 185.8 | 167.2 | 9.6 | 0.17 |
| Wean-estrus intervals, day | 4.7 | 4.8 | 0.4 | 0.98 | 7.6 | 4.4 | 1.1 | 0.18 | 4.2 | 5.7 | 0.9 | 0.35 |
| Sow BW change during lactation, lb | 15.3 | 3.6 | 3.5 | 0.04 | 8.5 | −0.9 | 9.8 | 0.53 | 1.8 | −1.1 | 7.5 | 0.73 |

| | Parity = 4 & 5 | | | | Parity = 6 & 7 | | | |
|---|---|---|---|---|---|---|---|---|
| Item | Control | therapeutic clay | PSE | P-value | Control | therapeutic clay | PSE | P-value |
| # of Trials | 1 | 1 | | | 1 | 1 | | |
| # of Sows | 33 | 31 | | | 37 | 23 | | |
| Parity | | | | | | | | |
| Total born | 15.7 | 16.1 | 0.5 | 0.44 | 14.1 | 16.3 | 0.5 | 0.03 |
| Born alive | 14.3 | 15.3 | 0.5 | 0.12 | 13.2 | 14.7 | 0.4 | 0.07 |
| Stillborns, % | 4.5 | 3.6 | 1.0 | 0.62 | 3.5 | 5.5 | 1.0 | 0.19 |
| Mummies, % | 3.5 | 1.5 | 0.8 | 0.07 | 2.4 | 3.3 | 0.7 | 0.49 |
| Total of stillborns and mummies, % | 8.0 | 5.3 | 1.3 | 0.15 | 5.9 | 8.8 | 1.2 | 0.17 |

TABLE 12-continued

Effect of parity on the response to feeding clay-based diets for the entire gestation + lactation period in sows

| | | | | | | | | |
|---|---|---|---|---|---|---|---|---|
| Litter birth weight, lb | 42.8 | 43.5 | 1.4 | 0.53 | 37.3 | 42.9 | 1.3 | 0.01 |
| Pig birth weight, lb | 3.03 | 2.98 | 0.08 | 0.87 | 2.79 | 3.02 | 0.07 | 0.07 |
| Pre-weaning mortality, % | 7.3 | 8.2 | 1.4 | 0.64 | 9.3 | 9.1 | 1.3 | 0.94 |
| Total number of piglet weaned | 13.4 | 14.2 | 0.4 | 0.19 | 11.9 | 13.3 | 0.4 | 0.06 |
| Pig weaning weight, lb | 12.2 | 12.6 | 0.3 | 0.21 | 12.3 | 11.4 | 0.3 | 0.08 |
| Litter weaning weight, lb | 160.8 | 171.6 | 6.1 | 0.09 | 145.0 | 149.1 | 5.7 | 0.67 |
| Wean-estrus intervals, day | 4.6 | 4.2 | 0.6 | 0.35 | 3.9 | 4.3 | 0.5 | 0.13 |
| Sow BW change during lactation, lb | 20.4 | 6.4 | 4.7 | 0.05 | 15.6 | 15.0 | 4.5 | 0.94 |

| | Parity ≥ 8 | | | |
|---|---|---|---|---|
| Item | Control | therapeutic clay | PSE | P-value |
| # of Trials | 1 | 1 | | |
| # of Sows | 10 | 19 | | |
| Parity | | | | |
| Total born | 12.3 | 14.4 | 1.0 | 0.02 |
| Born alive | 11.6 | 13.3 | 0.9 | 0.04 |
| Stillborns, % | 1.3 | 5.9 | 1.9 | 0.01 |
| Mummies, % | 3.2 | 1.4 | 1.4 | 0.30 |
| Total of stillborns and mummies, % | 4.5 | 7.3 | 2.4 | 0.20 |
| Litter birth weight, lb | 32.8 | 39.7 | 2.5 | 0.004 |
| Pig birth weight, lb | 2.68 | 2.95 | 0.14 | 0.05 |
| Pre-weaning mortality, % | 6.3 | 9.1 | 2.6 | 0.31 |
| Total number of piglet weaned | 9.8 | 11.5 | 0.8 | 0.10 |
| Pig weaning weight, lb | 11.9 | 11.4 | 0.5 | 0.26 |
| Litter weaning weight, lb | 131.9 | 139.5 | 11.0 | 0.41 |
| Wean-estrus intervals, day | 3.8 | 5.0 | 1.0 | 0.43 |
| Sow BW change during lactation, lb | 15.0 | −0.9 | 8.5 | 0.22 |

Example 6: Effect on Sows with Larger Litters

The data was re-analyzed in example 6 to determine the effectiveness of feeding clay-based diets to sows with greater than 15.5 pigs born alive (Table 13). These data suggest that born alive increased by 2% and that the number of pigs weaned increased by 0.7 pigs per litter (P=0.13). These data further illustrate that the effects of increasing litter size is not a function of lower sow performance (>15.5 pigs total born). Even in larger litter sizes feeding clay in gestation and lactation diets results in more pigs weaned.

TABLE 13A

Meta-analysis for feeding clay-based diets to high prolific sows for the entire gestation + lactation

| | Meta-analysis | | | |
|---|---|---|---|---|
| Item | Control | therapeutic clay | PSE | P-value |
| # of Trials | 2 | 2 | | |
| # of Sows | 105 | 129 | | |
| Parity | 5.3 | 5.1 | 0.2 | 0.47 |
| Total born | 16.9 | 17.2 | 0.2 | 0.28 |
| Born alive | 15.7 | 16.0 | 0.2 | 0.22 |
| Stillborn, % | 3.8 | 4.1 | 0.5 | 0.74 |
| Mummies, % | 3.3 | 2.9 | 0.5 | 0.55 |
| Stillborns + Mummies, % | 7.1 | 7.0 | 0.7 | 0.90 |
| Litter birth weight, lb | 44.7 | 45.2 | 0.7 | 0.57 |
| Pig birth weight, lb | 2.85 | 2.86 | 0.04 | 0.87 |
| Pre-weaning mortality, % | 11.3 | 10.7 | 1.2 | 0.43 |
| Total number of piglets weaned | 13.3 | 14.0 | 0.2 | 0.13 |
| Pig weaning weight, lb | 12.0 | 12.0 | 0.1 | 0.88 |
| Litter weaning weight, lb | 168.6 | 172.6 | 3.0 | 0.34 |
| Sow body weight change, lb | 7.0 | 0.2 | 2.8 | 0.09 |
| Wean-estrus intervals | 4.7 | 4.6 | 0.4 | 0.50 |

TABLE 13B

Meta-analysis for feeding clay-based diets to high prolific sows for the entire gestation + lactation

| | Parity = 2 | | | Parity = 3 | | | | |
|---|---|---|---|---|---|---|---|---|
| Item | Control | PSE | P-value | Control | therapeutic clay | PSE | P-value | Control |
| # of Trials | 2 | | | 2 | 2 | | | 2 |
| # of Sows | 105 | | | 9 | 22 | | | 14 |
| Parity | 5.3 | 0.2 | 0.47 | | | | | |
| Total born | 16.9 | 0.2 | 0.28 | 16.9 | 17.3 | 0.5 | 0.57 | 17.3 |
| Born alive | 15.7 | 0.2 | 0.22 | 15.5 | 16.0 | 0.5 | 0.49 | 16.3 |
| Stillborn, % | 3.8 | 0.5 | 0.74 | 5.6 | 4.8 | 1.5 | 0.71 | 2.8 |
| Mummies, % | 3.3 | 0.5 | 0.55 | 2.1 | 2.2 | 1.2 | 0.94 | 2.7 |
| Stillborns + Mummies, % | 7.1 | 0.7 | 0.90 | 7.7 | 7.1 | 1.9 | 0.82 | 5.4 |
| Litter birth weight, lb | 44.7 | 0.7 | 0.57 | 47.3 | 47.4 | 1.8 | 0.97 | 50.1 |
| Pig birth weight, lb | 2.85 | 0.04 | 0.87 | 3.02 | 2.98 | 0.10 | 0.76 | 3.13 |
| Pre-weaning mortality, % | 11.3 | 1.2 | 0.43 | 9.7 | 11.7 | 1.9 | 0.31 | 8.1 |
| Total number of piglets weaned | 13.3 | 0.2 | 0.13 | 14.4 | 13.7 | 0.4 | 0.17 | 14.7 |
| Pig weaning weight, lb | 12.0 | 0.1 | 0.88 | 11.8 | 12.1 | 0.4 | 0.53 | 13.0 |
| Litter weaning weight, lb | 168.6 | 3.0 | 0.34 | 162.9 | 178.8 | 8.4 | 0.19 | 193.1 |
| Sow body weight change, lb | 7.0 | 2.8 | 0.09 | −23.4 | −21.3 | 7.9 | 0.85 | −13.7 |
| Wean-estrus intervals | 4.7 | 0.4 | 0.50 | 4.9 | 6.0 | 0.5 | 0.77 | 6.3 |

TABLE 13C

Meta-analysis for feeding clay-based diets to high prolific sows for the entire gestation + lactation

| Item | Parity = 4 & 5 | | | | Parity = 6 & 7 | | | |
|---|---|---|---|---|---|---|---|---|
| | Control | therapeutic clay | PSE | P-value | Control | therapeutic clay | PSE | P-value |
| # of Trials | 2 | 2 | | | 2 | 2 | | |
| # of Sows | 35 | 29 | | | 27 | 27 | | |
| Parity | | | | | | | | |
| Total born | 17.1 | 17.5 | 0.3 | 0.35 | 17.0 | 17.9 | 0.3 | 0.05 |
| Born alive | 15.9 | 16.7 | 0.3 | 0.09 | 15.8 | 16.3 | 0.3 | 0.28 |
| Stillborn, % | 3.2 | 2.3 | 1.0 | 0.49 | 4.1 | 5.1 | 1.0 | 0.48 |
| Mummies, % | 3.6 | 2.8 | 0.8 | 0.47 | 2.6 | 3.4 | 0.9 | 0.51 |
| Stillborns + Mummies, % | 6.8 | 5.0 | 1.3 | 0.32 | 6.7 | 8.6 | 1.4 | 0.34 |
| Litter birth weight, lb | 45.7 | 44.0 | 1.2 | 0.30 | 41.7 | 43.4 | 1.3 | 0.34 |
| Pig birth weight, lb | 2.90 | 2.71 | 0.07 | 0.05 | 2.65 | 2.72 | 0.07 | 0.52 |
| Pre-weaning mortality, % | 7.3 | 8.8 | 1.7 | 0.60 | 10.0 | 11.6 | 1.7 | 0.59 |
| Total number of piglets weaned | 14.6 | 14.5 | 0.4 | 0.35 | 15.0 | 13.9 | 0.4 | 0.70 |
| Pig weaning weight, lb | 12.5 | 12.2 | 0.3 | 0.37 | 11.5 | 11.5 | 0.3 | 0.99 |
| Litter weaning weight, lb | 181.4 | 180.6 | 5.5 | 0.92 | 160.0 | 161.5 | 5.9 | 0.86 |
| Sow body weight change, lb | 12.8 | 5.2 | 5.0 | 0.28 | 18.2 | 13.4 | 5.5 | 0.53 |
| Wean-estrus intervals | 4.6 | 4.5 | 0.5 | 0.51 | 4.1 | 4.1 | 0.5 | 0.85 |

TABLE 13D

Meta-analysis for feeding clay-based diets to high prolific sows for the entire gestation + lactation

| Item | Parity ≥ 8 | | | | |
|---|---|---|---|---|---|
| | P-value | Control | therapeutic clay | PSE | P-value |
| # of Trials | | 2 | 2 | | |
| # of Sows | | 20 | 28 | | |
| Parity | | | | | |
| Total born | 0.05 | 16.4 | 16.4 | 0.4 | 0.93 |
| Born alive | 0.28 | 14.8 | 15.1 | 0.4 | 0.57 |
| Stillborn, % | 0.48 | 3.5 | 5.5 | 1.1 | 0.21 |
| Mummies, % | 0.51 | 5.5 | 2.8 | 1.0 | 0.04 |
| Stillborns + Mummies, % | 0.34 | 9.0 | 8.3 | 1.5 | 0.73 |
| Litter birth weight, lb | 0.34 | 38.7 | 41.7 | 1.4 | 0.13 |
| Pig birth weight, lb | 0.52 | 2.54 | 2.71 | 0.08 | 0.15 |
| Pre-weaning mortality, % | 0.59 | 12.9 | 12.5 | 1.9 | 0.35 |
| Total number of piglets weaned | 0.70 | 14.1 | 12.9 | 0.4 | 0.27 |
| Pig weaning weight, lb | 0.99 | 11.3 | 11.6 | 0.3 | 0.52 |
| Litter weaning weight, lb | 0.86 | 145.4 | 156.1 | 6.4 | 0.24 |
| Sow body weight change, lb | 0.53 | 40.9 | 18.8 | 6.0 | 0.01 |
| Wean-estrus intervals | 0.85 | 4.3 | 4.3 | 0.6 | 0.30 |

Example 7: Feeding Clay to Sows Improves Litter Size at Birth and at Weaning The effect of feeding Clay to sows during gestation and lactation was evaluated to determine the effect on reproductive performance. Sows (parity ≥2) were randomly selected from a commercial herd were allotted to either a Control diet (CON) or a diet containing Clay at 4.0 lb/ton, resulting in 97 sows for CON and 95 sows for Clay treatment. Dietary treatments started on day 3 after breeding and continued to the end of lactation through top-dressing clay to the basal diet (Table 14 and Table 15). Individual sow body weight was measured on the day when sows were transferred to the farrowing crate and at weaning to calculate body weight change during lactation period using the formula: Sow BW Change=Wean−(PRE−(LW+LW/5.5)), where Wean=sow weight at weaning; PRE=sow pre-farrow weight; LW=litter weight, LW/5.5=estimated placental weight. Lactation length and wean to estrus interval were recorded. The number of piglets born (alive and dead), individual pig birth weight (alive and dead), individual pig weaning weight, and the number of piglets dead during lactation were recorded for each litter. Cross-fostering and pull of starves were allowed within 2 days after birth and only within treatments or to the non-test litters. In addition, piglet management, including tail docking, iron injection, male piglet castration, were performed. Piglets' access to the sow feed was not restricted.

TABLE 14

Dietary composition of basal gestation diet

| Ingredient | Applewood Gestation[1], lb |
|---|---|
| Ground corn | 1,659.82 |
| SBM - HI PRO | 205.24 |
| Salt | 12.00 |
| Calcium Carbonate 38%/Unical S Lime | 24.99 |
| 21% Monocal | 31.63 |
| AA-L-Lysine HCL 78.8% | 5.21 |
| AA-Threonine | 2.09 |
| AA-Typtophan 100% | 0.32 |
| PHY 12 Optip D2000 M | 0.35 |
| NHF 5# Sow VTM w/choline | 5.00 |
| SalCURB | 6.50 |
| Difusion Plus - Promote | 5.00 |
| Choice white grease | 41.85 |
| Total | 2,000.00 |
| Nutrient Composition | |
| Crude Protein, % | 11.09 |
| Fat, % | 4.44 |
| Ash, % | 4.88 |
| NDF, % | 6.26 |
| ADF, % | 1.79 |
| Moisture, % | 13.87 |
| IV AA Dig, % | 0.89 |
| Particle score, unit | 72.20 |
| Calcium, % | 0.81 |
| Phosphorus, % | 0.60 |
| Ca/P Ratio | 1.35 |

[1]Diet was updated December 2018/January 2019.

TABLE 15

Dietary composition of basal lactation diet

| Ingredient | Applewood Lactation, lb |
|---|---|
| Corn - Fine Ground | 1,358.40 |
| SBM - Brewster | 526.26 |
| Salt | 9.50 |
| Calcium Carbonate 38% | 14.97 |
| Phosphate - mono dical | 23.96 |
| Fat - Fancy Tallow | 41.30 |
| AA-L-Lysine HCL 78.8% | 8.35 |
| Methionine-DL | 1.28 |
| AA-Threonine | 3.62 |
| Tryptophan 100% | 0.51 |
| PHY12 Optip D2000 M | 0.35 |
| NHF 5# Sow VTM w/ Choline | 5.00 |
| SALCURB | 6.50 |
| Total | 2,000.00 |
| Cost per ton | $ 219.83 |
| Nutrient, As Fed Conc | |
| Crude Protein, % | 18.02 |
| Fat, % | 4.12 |
| Ash, % | 4.71 |
| Calcium, % | 0.60 |

TABLE 15-continued

Dietary composition of basal lactation diet

| Ingredient | Applewood Lactation, lb |
|---|---|
| NDF, % | 6.23 |
| ADF, % | 1.98 |
| Moisture, % | 13.55 |
| IV AA Dig. % | 2.28 |
| Particle Score, unit | 59.09 |
| Phosphorus, % | 0.58 |
| Ca/P Ratio, ratio | 1.03 |
| SW NE, kcal/kg | 2,350.00 |
| Lysine, % | 1.28 |

[1]Diet updated 22 Feb. 2019.

Data was analyzed using ANOVA by the MIXED procedure of SAS. Sow/litter served as the experimental unit. The statistical model included fixed effect of dietary treatments and a covariate of parity. Multiple comparisons between treatments were performed using the Tukey adjustment option of SAS. All results were reported as least squares means. The significance level chosen was $\alpha=0.05$. Treatment effect was considered significant if $P<0.05$, whereas values between $0.05 \leq P \leq 0.10$ were considered as statistical trends.

Results from Table 16 suggest that sows fed clay had increased number of total-born pigs (P=0.15) and live born pigs (P=0.31) than the sows fed CON. Litter birth weight was greater (P=0.18) in Clay fed sows as a result of greater litter size. Pre-weaning mortality was lower (P=0.13), with less piglets lost due to low viability (P=0.09), in Clay fed sows compared with control fed sows. The improvement in total pigs born alive and pre-weaning livability resulted in greater number of pigs weaned (P=0.08) from Clay fed sows.

TABLE 16

Effects of feeding clay to sows during gestation and lactation on sow reproductive performance

| | Control | Clay | SE | P-value |
|---|---|---|---|---|
| # of Sows | 97 | 95 | | |
| Parity[1] | 5.7 | 6.2 | 0.3 | 0.24 |
| Conception rate, % | 99.2 | 98.5 | N/A | 0.95 |
| Farrowing rate, % | 92.3 | 89.2 | N/A | 0.79 |
| Total born | 15.1 | 15.7 | 0.5 | 0.15 |
| Born alive | 13.1 | 13.4 | 0.4 | 0.31 |
| Stillborns, % | 8.7 | 9.6 | 1.0 | 0.48 |
| Mummies, % | 5.3 | 5.1 | 0.8 | 0.95 |
| Litter birth weight, lb | 36.5 | 37.8 | 1.2 | 0.18 |
| Pig birth weight,[2] lb | 2.74 | 2.81 | 0.06 | 0.27 |
| Low birth weight (<1.5 lb), % | 3.9 | 3.8 | N/A | 0.87 |
| Medium birth weight (1.5-3.0 lb), % | 55.3 | 53.4 | N/A | 0.51 |
| High birth weight (>3.0 lb), % | 40.8 | 42.8 | N/A | 0.42 |
| Pre-weaning mortality, % | 6.2 | 4.4 | 1.2 | 0.13 |
| Piglets lost due to low viability, % | 2.0 | 0.8 | 0.7 | 0.09 |
| Total wean | 12.2 | 12.8 | 0.4 | 0.08 |
| Lactation length, day | 19.8 | 19.6 | 0.3 | 0.45 |
| Pig weaning weight,[3] lb | 11.5 | 11.6 | 0.2 | 0.95 |
| Litter weaning weight,[3] lb | 138.7 | 145.9 | 5.7 | 0.21 |
| Wean-estrus intervals, day | 5.2 | 4.3 | 0.5 | 0.15 |

TABLE 16-continued

Effects of feeding clay to sows during gestation and lactation on sow reproductive performance

|  | Control | Clay | SE | P-value |
|---|---|---|---|---|
| Sow BW prior to farrow, lb | 587 | 600 | 6 | 0.02 |
| Sow BW change during lactation,[3,4] lb | 5.8 | 1.1 | 3.5 | 0.26 |
| Sow feed intake during lactation |  |  |  |  |
| # of Sows |  |  |  |  |
| ADFI during lactation, lb/day | 11.1 | 11.7 | 0.5 | 0.62 |

[1]Parity was used as covariate in all analyses
[2]Born alive was used as covariate
[3]Lactation length was used as covariate
[4]Sow BW prior to farrowing was used as covariate

Example 8: Meta-Analysis of Three Clay Sow Studies

Three experiments were conducted following the same procedure to evaluate the effects of feeding clay to sows during gestation and lactation on sow reproductive performance. In each experiment, sows (parity ≥2) randomly selected from the commercial herd were allotted to either a Control diet (CON) or a diet containing clay at 4.0 lb/ton, resulting in a total of 294 sows for CON and 302 sows for clay treatment over three experiments. Experimental diets were fed from day 3 of gestation and continued to the end of lactation. Data from the three experiments were compiled for meta-analysis using the MIXED procedure of SAS.

Data from Table 17 suggest that feeding clay to sows during gestation and lactation improved (P<0.05) total born, born alive, and number of pigs weaned compared to pigs fed the control diet. Litter weight at birth and at weaning were also improved (P<0.05) as a result of improved litter size at birth and at weaning.

TABLE 17

Meta-analysis of three sow studies fed Clay during entire gestation and lactation
Table 17. Meta-analysis of three sow studies fed Clay during entire gestation and lactation

| | Meta-analysis (by trial) | | | | |
|---|---|---|---|---|---|
| Item | Control | Clay | % Change | PSE | P-value |
| # of Trials | 3 | 3 | | | |
| # of Sows | 294 | 302 | | | |
| Parity | 5.7 | 5.7 | | 0.2 | 1.00 |
| Total born | 14.1 | 14.9 | 5.7% | 0.3 | 0.002 |
| Born alive | 12.5 | 13.1 | 4.6% | 0.3 | 0.01 |
| Stillborn, % | 6.59 | 7.72 | 17.0% | 0.67 | 0.03 |
| Mummies, % | 4.24 | 4.38 | 3.3% | 0.57 | 0.74 |
| Stillborns + Mummies, % | 10.8 | 12.1 | 11.7% | 0.9 | 0.07 |
| Litter birth weight, lb | 36.0 | 37.5 | 4.2% | 0.8 | 0.02 |
| Pig birth weight, lb | 2.78 | 2.81 | 1.2% | 0.05 | 0.33 |
| % of pigs with birth weight < 1.7 lb | 6.8 | 6.0 | -12.6% | N/A | 0.12 |
| Pre-weaning mortality, % | 7.1 | 6.6 | -6.5% | 0.9 | 0.51 |
| Total number of piglet weaned | 11.5 | 12.2 | 5.5% | 0.3 | 0.004 |
| Pig weaning weight, lb | 12.2 | 12.2 | 0.6% | 0.2 | 0.59 |
| Litter weaning weight, lb | 139.7 | 147.1 | 5.3% | 3.9 | 0.01 |
| Sow body weight change, lb | 13.7 | 8.6 | -37.7% | 3.1 | 0.03 |
| Wean-estrus intervals | 4.4 | 4.3 | -1.1% | 0.4 | 0.85 |

| | 2014-006 | | | P-value |
|---|---|---|---|---|
| Item | Control | Clayt | PSE | |
| # of Trials | 1 | 1 | | |
| # of Sows | 97 | 102 | | |
| Parity | 6.1 | 5.8 | 0.3 | 0.42 |
| Total born | 14.1 | 14.7 | 0.4 | 0.15 |
| Born alive | 13.3 | 13.6 | 0.4 | 0.37 |
| Stillborn, % | 3.23 | 4.36 | 0.67 | 0.13 |
| Mummies, % | 2.00 | 2.87 | 0.65 | 0.24 |
| Stillborns + Mummies, % | 5.2 | 7.2 | 1.0 | 0.09 |
| Litter birth weight, lb | 38.6 | 39.0 | 1.0 | 0.72 |
| Pig birth weight, lb | 2.94 | 2.91 | 0.05 | 0.63 |
| % of pigs with birth weight < 1.7 lb | 7.1 | 6.8 | N/A | 0.77 |
| Pre-weaning mortality, % | 7.8 | 8.1 | 1.1 | 0.84 |
| Total number of piglet weaned | 12.2 | 12.5 | 0.3 | 0.39 |
| Pig weaning weight, lb | 12.5 | 12.8 | 0.2 | 0.12 |
| Litter weaning weight, lb | 150.5 | 158.2 | 4.1 | 0.09 |
| Sow body weight change, lb | 9.6 | 10.9 | 3.9 | 0.77 |
| Wean-estrus intervals | 4.3 | 4.6 | 0.2 | 0.26 |

| | 2017-006 | | | P-value |
|---|---|---|---|---|
| Item | Control | Clayt | PSE | |
| # of Trials | 1 | 1 | | |
| # of Sows | 100 | 105 | | |
| Parity | 5.1 | 5.0 | 0.2 | 0.64 |
| Total born | 14.0 | 15.2 | 0.4 | 0.005 |
| Born alive | 13.0 | 14.2 | 0.3 | 0.005 |
| Stillborn, % | 3.35 | 4.52 | 0.75 | 0.17 |
| Mummies, % | 2.29 | 1.92 | 0.57 | 0.55 |
| Stillborns + Mummies. % | 5.6 | 6.4 | 1.0 | 0.46 |
| Litter birth weight. lb | 39.6 | 42.9 | 1.0 | 0.003 |
| Pig birth weight, lb | 2.99 | 3.08 | 0.05 | 0.12 |
| % of pigs with birth weight <1.7 lb | 6.6 | 4.9 | N/A | 0.06 |
| Pre-weaning mortality, % | 8.4 | 8.6 | 1.0 | 0.82 |
| Total number of piglet weaned | 11.9 | 12.9 | 0.3 | 0.007 |
| Pig weaning weight, lb | 12.0 | 11.8 | 0.2 | 0.43 |
| Litter weaning weight. lb | 144.6 | 152.3 | 4.6 | 0.13 |
| Sow body weight change, lb | 13.3 | 5.3 | 3.4 | 0.04 |

TABLE 17-continued

Meta-analysis of three sow studies fed Clay during entire gestation and lactation
Table 17. Meta-analysis of three sow studies fed Clay during entire gestation and lactation

| | | | | |
|---|---|---|---|---|
| Wean-estrus intervals | 4.7 | 4.7 | 0.4 | 0.95 |

| | 2019-001 | | | P-value |
|---|---|---|---|---|
| Item | Control | Clayt | PSE | |
| # of Trials | 1 | 1 | | |
| # of Sows | 97 | 95 | | |
| Parity | 5.7 | 6.2 | 0.3 | 0.24 |
| Total born | 14.6 | 15.3 | 0.5 | 0.15 |
| Born alive | 12.8 | 13.2 | 0.4 | 0.31 |
| Stillborn, % | 7.76 | 8.51 | 1.09 | 0.48 |
| Mummies, % | 4.82 | 4.76 | 0.96 | 0.95 |
| Stillborns + Mummies, % | 12.6 | 13.3 | 1.4 | 0.62 |
| Litter birth weight. lb | 35.5 | 37.1 | 1.2 | 0.18 |
| Pig birth weight, lb | 2.67 | 2.74 | 0.07 | 0.27 |
| % of pigs with birth weight < 1.7 lb | 6.8 | 6.3 | N/A | 0.63 |
| Pre-weaning mortality, % | 6.6 | 4.7 | 1.3 | 0.13 |
| Total number of piglet weaned | 11.8 | 12.6 | 0.5 | 0.07 |
| Pig weaning weight, lb | 11.5 | 11.5 | 0.2 | 0.95 |
| Litter weaning weight, lb | 136.4 | 144.0 | 6.6 | 0.21 |

TABLE 17-continued

Meta-analysis of three sow studies fed Clay during entire gestation and lactation
Table 17. Meta-analysis of three sow studies fed Clay during entire gestation and lactation

| | | | | |
|---|---|---|---|---|
| Sow body weight change, lb | 1.1 | −3.2 | 3.8 | 0.26 |
| Wean-estrus intervals | 5.2 | 4.4 | 0.6 | 0.18 |

Total fecal amino acid concentration was reduced (P<0.01) for sows fed clay verses control fed sows. In a review from Dai et al., (2015), the prevailing information suggests that amino acid recycling is increased during pregnancy, triggering improvements in fetal implantation. The regression analyses below suggest that reduced fecal amino acid levels enhance piglet survival post-farrowing and weight gain during lactation. Reduced amino acid levels also is indicative of reduced ammonia production, which is favorable to improving embryo survival (Dai et al., 2015). Taken together these data suggest that the improved amino acid utilization of reduced fecal amino acid concentrations are related to improvements in signaling to promote pregnancy and reduce fetal exposure to toxins like ammonia and nitric oxide. Sows fed clay had improved amino acid utilization further reducing the exposure to the toxic effects of high ammonia production. The data in Table 18 further suggests that short chain fatty acid concentrations are reduced in the feces of clay fed sows. Dai (2015) further suggests that reduced short chain fatty acids improves insulin sensitivity, which is related to improved fetal survival and post weaning development.

TABLE 18

Metabolites in sow feces (end of gestation)

| Item | Control | Clay | SE | P-value | % change |
|---|---|---|---|---|---|
| # of sows analyzed for fecal metabolites | 16 | 16 | | | |
| Parity | 5.75 | 6.31 | 0.66 | 0.55 | |
| Reproductive performance of sampling sows | | | | | |
| Total born | 15.2 | 16.1 | 0.7 | 0.34 | |
| Born alive | 12.6 | 13.6 | 0.7 | 0.34 | |
| Pig birth weight, lb | 3.0 | 3.0 | 0.1 | 0.90 | |
| PWM. % | 8.7 | 4.9 | 2.7 | 0.32 | |
| Total wean | 12.2 | 12.9 | 0.7 | 0.53 | |
| Pig wean weight. lb | 11.6 | 12.1 | 0.5 | 0.45 | |
| Sow fecal metabolites end of gestation[1] | | | | | |
| Fatty acids in feces. mg/g | | | | | |
| acetic acid | 4.58 | 3.28 | 0.49 | 0.09 | −28% |
| propionic acid | 3.69 | 2.46 | 0.45 | 0.07 | −33% |
| butyric acid | 1.99 | 1.27 | 0.25 | 0.07 | −36% |
| valeric acid | 0.586 | 0.375 | 0.072 | 0.06 | −36% |
| isovaleric acid | 0.173 | 0.128 | 0.020 | 0.13 | −26% |
| Total SCFA | 11.00 | 7.53 | 1.23 | 0.07 | −32% |
| C6:0 | 0.019 | 0.014 | 0.006 | 0.54 | −26% |
| C8:0 | 0.0059 | 0.0056 | 0.0005 | 0.67 | −5% |
| C14:0 | 0.125 | 0.127 | 0.018 | 0.93 | 2% |
| C15:0 | 0.090 | 0.178 | 0.027 | 0.01 | 98% |
| C16:0 | 0.881 | 1.086 | 0.075 | 0.08 | 23% |
| C16:1 | 0.017 | 0.013 | 0.001 | 0.08 | −22% |
| C18:0 | 0.336 | 0.451 | 0.028 | 0.009 | 34% |
| C18:1 | 0.606 | 0.723 | 0.113 | 0.47 | 19% |

TABLE 18-continued

Metabolites in sow feces (end of gestation)

| Item | Control | Clay | SE | P-value | % change |
|---|---|---|---|---|---|
| Bile acids in feces. ug/g | | | | | |
| Cholic acid | 9.52 | 9.48 | 0.20 | 0.88 | 0% |
| Chenodeoxycholic acid | 0.64 | 0.66 | 0.13 | 0.92 | 3% |
| Lithocholic acid | 870 | 413 | 104 | 0.007 | −52% |
| Hyodeoxycholic acid | 1311 | 240 | 178 | 0.001 | −82% |
| Total bile acids | 2153 | 719 | 246 | 0.001 | −67% |
| Amino acids in feces. ug/g | | | | | |
| Alanine | 161 | 50 | 17 | 0.0007 | −69% |
| Arginine | 26.0 | 10.0 | 6.3 | <.0001 | −61% |
| Asparagine | 2.46 | 1.63 | 1.14 | 0.01 | −34% |
| Aspartic acid | 35.6 | 47.8 | 5.5 | 0.14 | 34% |
| Citrulline | 47.7 | 37.1 | 6.1 | 0.22 | −22% |
| Glutamic acid | 564 | 461 | 68 | 0.29 | −18% |
| Glutamine | 9.87 | 7.83 | 0.48 | 0.01 | −21% |
| Glycine | 41.0 | 27.3 | 8.9 | 0.07 | −33% |
| Histidine | 8.41 | 8.06 | 0.57 | 0.67 | −4% |
| Leucine/Isoleucine | 77.9 | 22.2 | 7.6 | 0.0001 | −71% |
| Lysine | 85.5 | 70.4 | 8.2 | 0.21 | −18% |
| Methionine | 23.8 | 11.8 | 2.5 | 0.005 | −50% |
| Ornithine | 6.40 | 7.61 | 1.05 | 0.43 | 19% |
| Phenylalanine | 92.3 | 9.3 | 11.3 | 0.0001 | −90% |
| Proline | 41.8 | 14.7 | 5.8 | 0.005 | −65% |
| r-amino-n-butyric acid | 5.1 | 12.3 | 3.2 | 0.004 | 141% |
| Serine | 56.5 | 38.0 | 4.9 | 0.02 | −33% |
| Taurine | 1.83 | 0.31 | 0.58 | 0.08 | −83% |
| Threonine | 42.9 | 22.0 | 3.2 | 0.0004 | −49% |
| Tryptophan | 7.9 | 2.7 | 1.0 | 0.002 | −65% |
| Tyrosine | 73.0 | 11.7 | 9.6 | 0.0005 | −84% |
| Valine | 77.1 | 27.5 | 8.8 | 0.001 | −64% |
| Total amino acids | 1490 | 935 | 142 | 0.01 | −37% |

Linear Regression Analysis to Build Prediction Equation for PWM and Pig Weaning Wt Pig Weaning Weight was Predicted Using the Following Equation:

Pig weaning weight (Control)=$a_{2-11}$×Parity(2-11)+ 1.123×weaning age−0.00083×Total AA in sow feces end of gestation (μg/g)−0.0215×birth weight (lb)−11.945

Pig weaning weight (clay)=$a_{2-11}$×Parity(2-11)+ 1.123×weaning age−0.00201×Total AA in sow feces end of gestation (μg/g)+3.342×birth weight (lb)−19.626

$R^2$=0.82

This equation suggests that the total AA concentration in sow feces collected at the end of gestation had negative correlation with pig weaning weight in both treatments. Pig weaning weight from sows fed clay had (0.00201−0.00083)/0.00083=142% greater impact from total AA concentration in sow feces compared with Control.

Pre-Weaning Mortality was Predicted Using the Following Equation:

Pre-weaning mortality (Control)=$a_{2-11}$×Parity (2-11)+1.323×Total SCFA in sow feces−10.601

Pre-weaning mortality (clay)=$a_{2-11}$×Parity (2-11)+ 0.337×Total SCFA in sow feces−1.463

$R^2$=0.59

This equation suggests that the total SCFA concentration in sow feces collected at the end of gestation had positive correlation with pig PWM in both treatments. Pig PWM from sows fed day had (1.323−0.337)/1.323=75% less impact from total SCFA concentration in sow feces compared with Control.

Example 9: Feeding Clay to Sows Improved Concentration of Total Immunoglobins in their Offspring The immunocrit measures total immunoglobulins in blood, which is the protein that recognizes bacteria and other agents that can cause diseases. When piglets are born, they have very little immunoglobulin concentration (essentially zero). Thus, all the immunoglobulin in blood from a newborn piglet comes from the sow by way of colostrum intake. Therefore, the immunocrit measure can determine if a piglet has received enough colostrum. Previous results have indicated that an immunocrit value at birth below 0.05 is associated with greater risk of preweaning mortality due to insufficient colostrum intake. In this experiment, a total of 37 piglets from sows fed a control diet and 50 piglets from sows fed a diet containing Clay at 4.0 lb/ton during gestation and lactation were used to evaluate the immunocrit values on day 2 after birth and at weaning.

Results from Table 19 show that piglets from sows fed Clay had 5.9% greater immunocrit value on day 2 after birth (P=0.44) compared with piglets from sows fed control diet. Approximately 44% less pigs from sows fed Clay with immunocrit <0.05 at birth suggest a greater colostrum intake and higher immunoglobins concentration compared with pigs from sows fed control diet. In addition, the greater immunocrit value at weaning (7.0% increase) in a litter from sows fed Clay indicate a better immune status and potentially better health status and growth performance in later growing phases after weaning.

TABLE 19

Immunocrit values of piglets from sows fed Control diet and diet containing Clay at 4.0 lb/ton

| Item | Control | Clay | SE | P-value | % Change over Control |
|---|---|---|---|---|---|
| Piglet Immunocrit | | | | | |
| # of pigs measured | 37 | 50 | | | |
| # of litters measured | 20 | 25 | | | |
| Immunocrit on Day 2 after birth | 0.095 | 0.101 | 0.005 | 0.44 | +5.9% |
| % of pigs with Immunocrit <0.05 | 10.8 | 6.0 | N/A | 0.43 | −44% |
| Immunocrit at weaning | 0.040 | 0.043 | 0.002 | 0.25 | +7.0% |

Example 10: Feeding Clay to Sows Improved Livability of their Offspring from Birth to Market A study was conducted to evaluate the effects of feeding Clay to sows during gestation and lactation on livability of their offspring from birth to market. A total of 352 pigs from sows fed a control diet and 143 pigs from sows fed Clay at 4.0 lb/ton were individually identified using ear tags and tracked from nursery to market. Removal rate from nursery to market, and percentage of light pigs were lower (P=0.88 and P=0.06, respectively) in pigs from sows fed Clay, resulting in more pigs marketed at the primary market compared with pigs from sows fed control diet (93.0 vs. 88.6%; Table 20). Taken together the data shown in Example 1, feeding Clay to sows resulted in 0.6 more pigs per litter at weaning and 1.1 more pigs per litter marketed at the primary market due to greater livability from birth to market compared with pigs fed control diet.

TABLE 20

Birth to market livability of piglets from sows fed Control diet and diet containing Clay

| Sow Treatment | Control | Clay | P-value |
|---|---|---|---|
| Nursery phase | | | |
| # of pigs start | 352 | 143 | |
| Mortality, % | 0.85 | 0.70 | 0.58 |
| Removal (mortality + fallbacks), % | 6.5 | 4.9 | 0.75 |
| Grow-finish phase | | | |
| Mortality, % Nursery to market | 2.3 | 2.1 | 0.84 |
| Removal (mortality + fallbacks), % | 8.8 | 7.0 | 0.88 |
| Light + Junk pigs, % | 2.6 | 0.0 | 0.06 |
| Pigs to the primary market, % | 88.6 | 93.0 | 0.97 |
| Birth to market | | | |
| Total born/litter | 15.1 | 15.7 | 0.15 |
| Born alive/litter | 13.1 | 13.4 | 0.31 |
| Total wean/litter | 12.2 | 12.8 | 0.08 |
| Pigs to the primary market/litter | 10.8 | 11.9 | |

What is claimed is:

1. A method of improving reproductive and litter performance of a maternal animal, the method comprising, orally administering to the animal an effective amount of a therapeutic clay, wherein the therapeutic clay is a K-rectorite.

2. The method of claim 1, wherein the K-rectorite comprises therapeutic effective amounts of a reducing agent.

3. The method of claim 1, wherein the clay is formulated in a feed composition for oral administration to the animal.

4. The method of claim 1, wherein the clay is administered during gestation, during lactation, and combinations thereof.

5. The method of claim 1, wherein the clay is administered for a period of time during gestation.

6. The method of claim 1, wherein the clay is administered from breeding until farrowing.

7. The method of claim 1, wherein the clay is administered for a period of time during lactation.

8. The method of claim 1, wherein the clay is administered from farrowing until weaning.

9. The method of claim 1, wherein improving reproductive performance comprises reducing embryonic loss, increasing litter size, increasing the number of live births, improving the immune status of the maternal animal, reducing the concentration of maternal fecal amino acids, reducing the concentration of maternal fecal short-chained amino acid, and increasing litter birth weight.

10. The method of claim 9, wherein improving the immune status of the maternal animal comprises an increased level of IFNγ and TNF-α in the maternal animal, and decreased levels of TRAIL in the maternal animal.

11. The method of claim 10, wherein the level of pre-farrowing TNF-α in the maternal animal is positively correlated with total wean, negatively correlated with subsequent stillborns, and positively correlated with subsequent mummies.

12. The method of claim 10, wherein the level of pre-farrowing TRAIL is negatively correlated with subsequent total born and subsequent born alive.

13. The method of claim 10, wherein the level of wean IFN-γ is positively correlated with total wean.

14. The method of claim 1, wherein improving litter performance comprises increasing amount of young animal colostrum intake, reducing young animal pre-weaning mortality, reducing the number of young animals lost due to low viability, reducing the number of weaned young animals, improving the immune status of young animals at weaning, reducing the number of lightweight young animals from nursery to market, increasing the number of young animals marketed per sow, and increasing calculated litter weight gain.

15. The method of claim 1, wherein the animal is a pig.

16. The method of claim 15, wherein the amount of clay in a feed composition ranges from about 0.1 lb/ton to 10 lb/ton.

17. The method of claim 15, wherein the amount of clay in a gestation feed composition ranges from about 0.5 lb/ton to 4.0 lb/ton.

18. The method of claim 15, wherein the amount of clay in a lactation feed composition ranges from about 0.5 lb/ton to 1.5 lb/ton.

19. The method of claim 15, wherein the amount of clay administered to a sow ranges from about 1.0 g/d to about 10 g/d.

20. The method of claim 15, wherein the amount of clay administered to an animal ranges from about 0.1 g/d to about 8 g/d.

* * * * *